(12) United States Patent
Ingemarsson-Matzen

(10) Patent No.: US 9,545,331 B2
(45) Date of Patent: Jan. 17, 2017

(54) INCREMENTAL AND/OR SUCCESSIVE ADJUSTABLE MANDIBULAR ADVANCEMENT DEVICE FOR PREVENTING AND TREATMENT OF SNORING AND OBSTRUCTIVE SLEEP APNEA

(71) Applicant: Natashia Ingemarsson-Matzen, Charlottenlund (DK)

(72) Inventor: Natashia Ingemarsson-Matzen, Charlottenlund (DK)

(73) Assignee: Petruska, LLC, Orlando, FL (US)

( * ) Notice: Subject to any disclaimer, the term of this patent is extended or adjusted under 35 U.S.C. 154(b) by 0 days.

(21) Appl. No.: 14/011,117

(22) Filed: Aug. 27, 2013

(65) Prior Publication Data
US 2014/0352700 A1    Dec. 4, 2014

(30) Foreign Application Priority Data

Jun. 2, 2013 (DK) ............................... 2013 00338

(51) Int. Cl.
*A61F 5/56* (2006.01)
*A61C 7/08* (2006.01)

(52) U.S. Cl.
CPC ....... *A61F 5/566* (2013.01); *A61C 7/08* (2013.01)

(58) Field of Classification Search
CPC ....................................................... A61F 5/566
USPC ................................................. 128/848, 846
See application file for complete search history.

(56) References Cited

U.S. PATENT DOCUMENTS

| D273,893 | S | 5/1984 | Weitzman |
| D295,218 | S | 4/1988 | Kwok |
| 5,313,960 | A | 5/1994 | Tomasi |
| D358,889 | S | 5/1995 | Wong |
| 6,729,335 | B1 | 5/2004 | Halstrom |
| D492,785 | S | 7/2004 | Garabito |
| D529,615 | S | 10/2006 | Atz |
| D554,260 | S | 10/2007 | Diacopoulos |
| D604,854 | S | 11/2009 | McDonald |
| D621,942 | S | 8/2010 | Massad |
| 7,810,502 | B1 | 10/2010 | Nguyen et al. |

(Continued)

FOREIGN PATENT DOCUMENTS

| AU | 1999 476 15 B2 | 1/2000 |
| CA | 223 650 3 A1 | 11/1998 |

(Continued)

OTHER PUBLICATIONS

Design U.S. Appl. No. 29/430,427, Applicant: Natashia Ingemarsson-Matzen.

(Continued)

*Primary Examiner* — Tarla Patel

(57) ABSTRACT

The current invention relates to an adjustable mandibular advancement device with a unique combination of resilient hinging, dentition engagement and adjustability, to prevent or reduce Snoring and/or Obstructive Sleep Apnea Syndrome. The adjustability is described by means of two concepts of adjustability for the relative enlargement or diminution of the members of the device, incremental and successive advancement mechanisms, in either combination or separately. By use of thermoplastic materials the device can be used in the outmost variability of the human dentition.

10 Claims, 49 Drawing Sheets

(56) References Cited

U.S. PATENT DOCUMENTS

| | | |
|---|---|---|
| D632,395 S | 2/2011 | Massad |
| D642,277 S | 7/2011 | Farrell |
| D654,173 S | 2/2012 | Farrell |
| D710,506 S | 8/2014 | Tolentino |
| D717,449 S | 11/2014 | Farrell |
| D722,171 S | 2/2015 | Bergersen |
| D739,029 S | 9/2015 | Bergersen |
| 2005/0236003 A1 | 10/2005 | Meader |
| 2008/0099029 A1 | 5/2008 | Lamberg |
| 2008/0115791 A1 | 5/2008 | Heine |
| 2009/0014013 A1 | 1/2009 | Magnin |
| 2010/0043805 A1 | 2/2010 | Kelly |
| 2010/0300458 A1 | 12/2010 | Stubbs et al. |
| 2011/0017220 A1 | 1/2011 | Lindsay et al. |
| 2011/0226261 A1 | 9/2011 | Hernandez |
| 2012/0024297 A1* | 2/2012 | Hegde et al. ............ 128/848 |
| 2013/0014765 A1 | 1/2013 | Meade |
| 2013/0098372 A1* | 4/2013 | Webster et al. ......... 128/848 |
| 2013/0263865 A1* | 10/2013 | Khast ..................... 128/848 |
| 2014/0352700 A1 | 12/2014 | Ingemarsson-Matzen |
| 2014/0352701 A1 | 12/2014 | Ingemarsson-Matzen |

FOREIGN PATENT DOCUMENTS

| | | |
|---|---|---|
| DE | 201 02 432 U1 | 4/2001 |
| EP | 0 312 368 | 4/1989 |
| EP | 0 337 201 B1 | 8/1992 |
| EP | 0 794 749 B1 | 6/2003 |
| EP | 1 719 481 A1 | 4/2009 |
| EP | 2 529 710 A1 | 12/2012 |
| EP | 2 491 901 A1 | 7/2014 |
| GB | 2 264 868 | 9/1993 |
| WO | WO 92/05752 | 4/1992 |
| WO | WO 92/11827 | 7/1992 |
| WO | WO 01 302 60 A1 | 5/2001 |
| WO | WO 2008 / 130 413 A1 | 10/2008 |
| WO | WO 2009 / 062 541 A1 | 5/2009 |
| WO | WO 2011 / 115 962 A1 | 9/2011 |
| WO | WO 2013 / 032 884 A1 | 3/2013 |
| WO | WO 2013 049 751 A2 | 4/2013 |
| WO | WO/2014/194910 | 12/2014 |

OTHER PUBLICATIONS

Design U.S. Appl. No. 29/536,338, Applicant: Natashia Ingemarsson-Matzen.

Industrial Design U.S. Appl. No. 35/500,086, Applicant: Natashia Ingemarsson-Matzen.

* cited by examiner

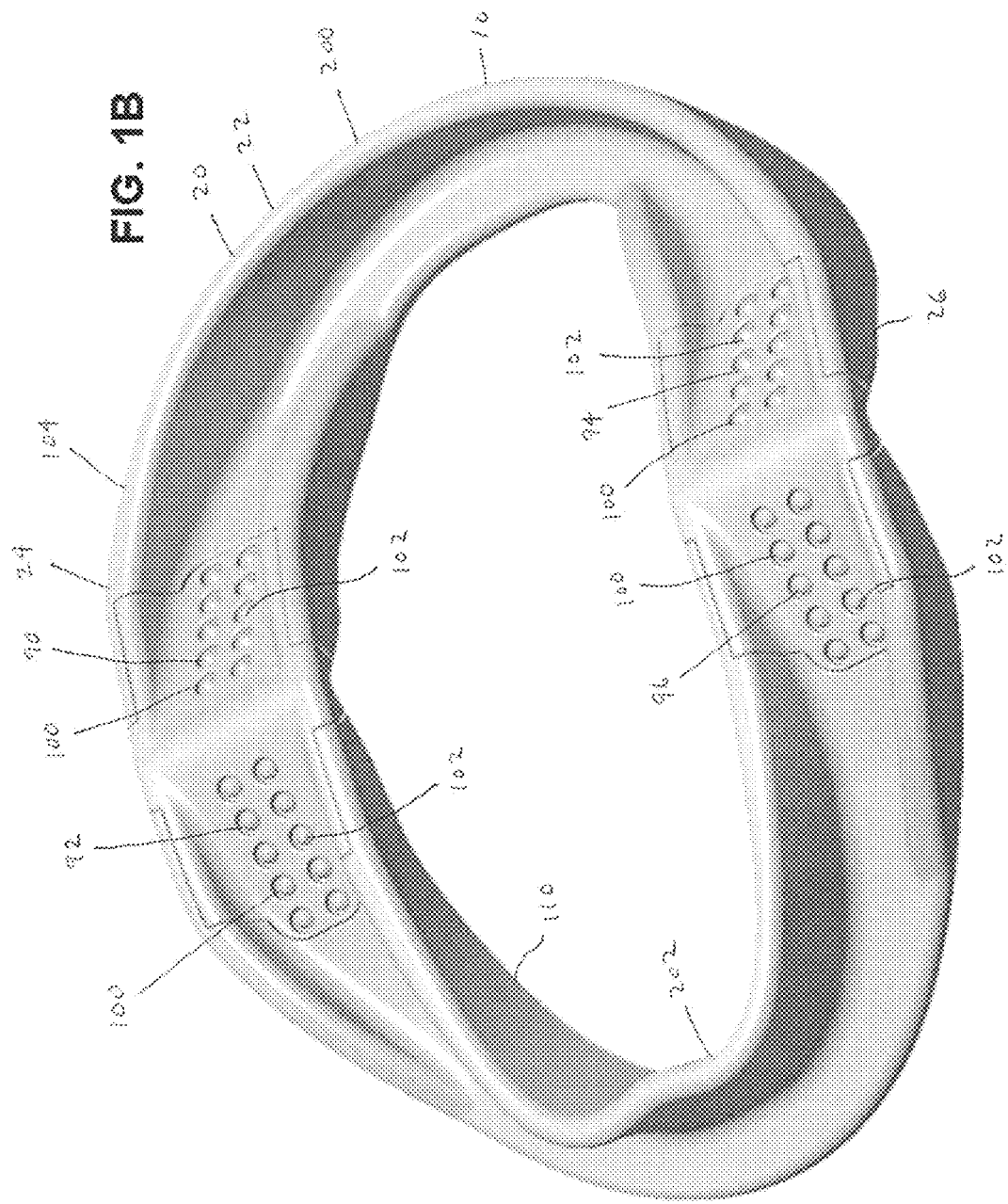

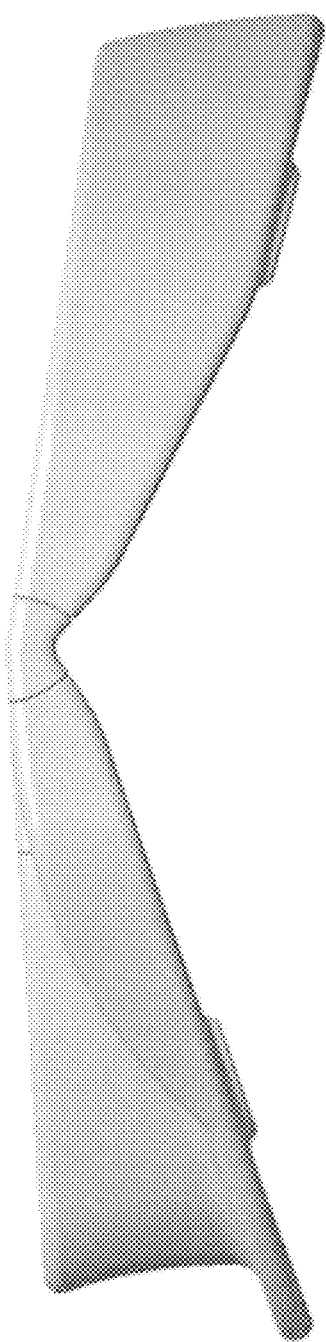

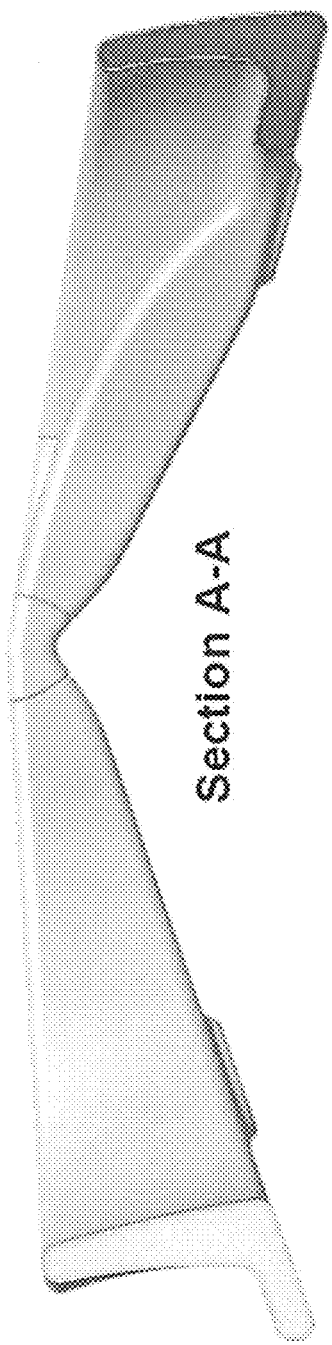

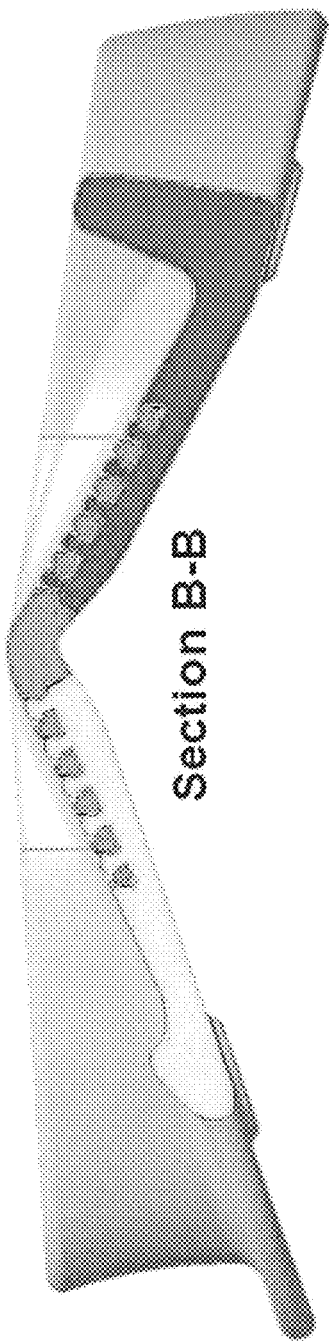

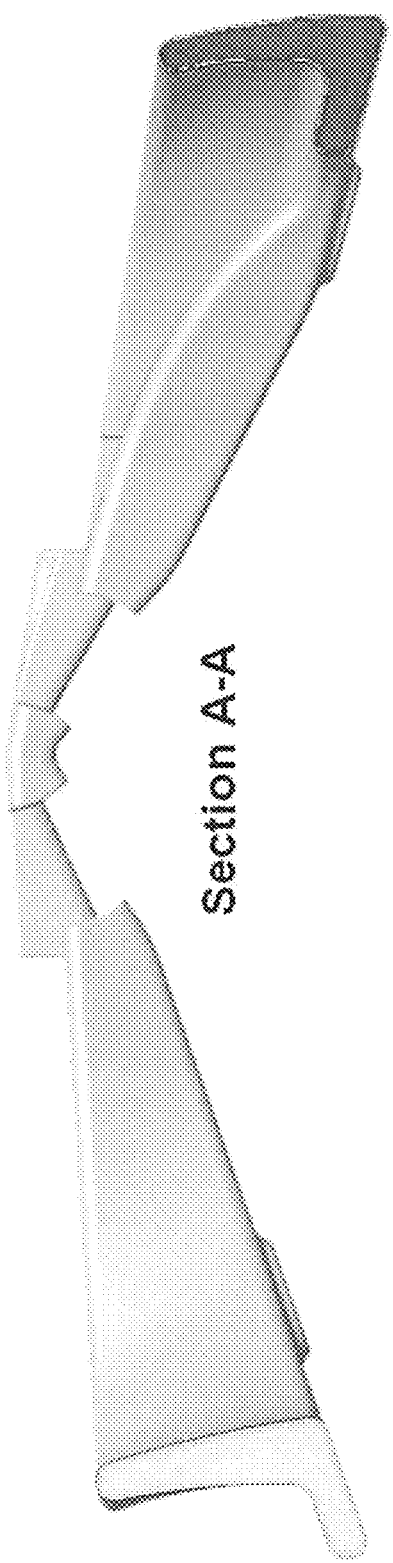

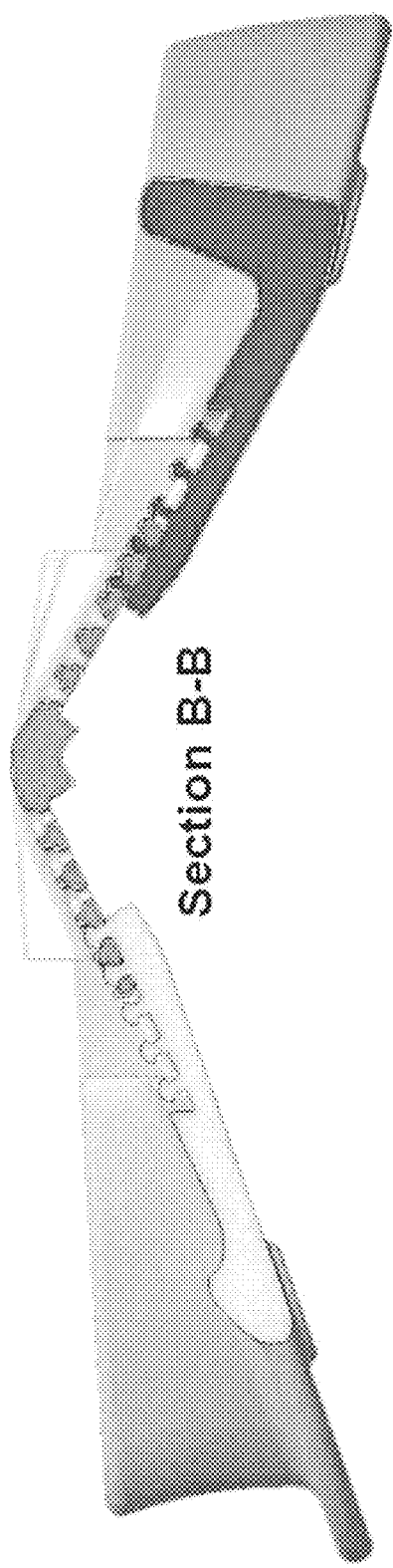

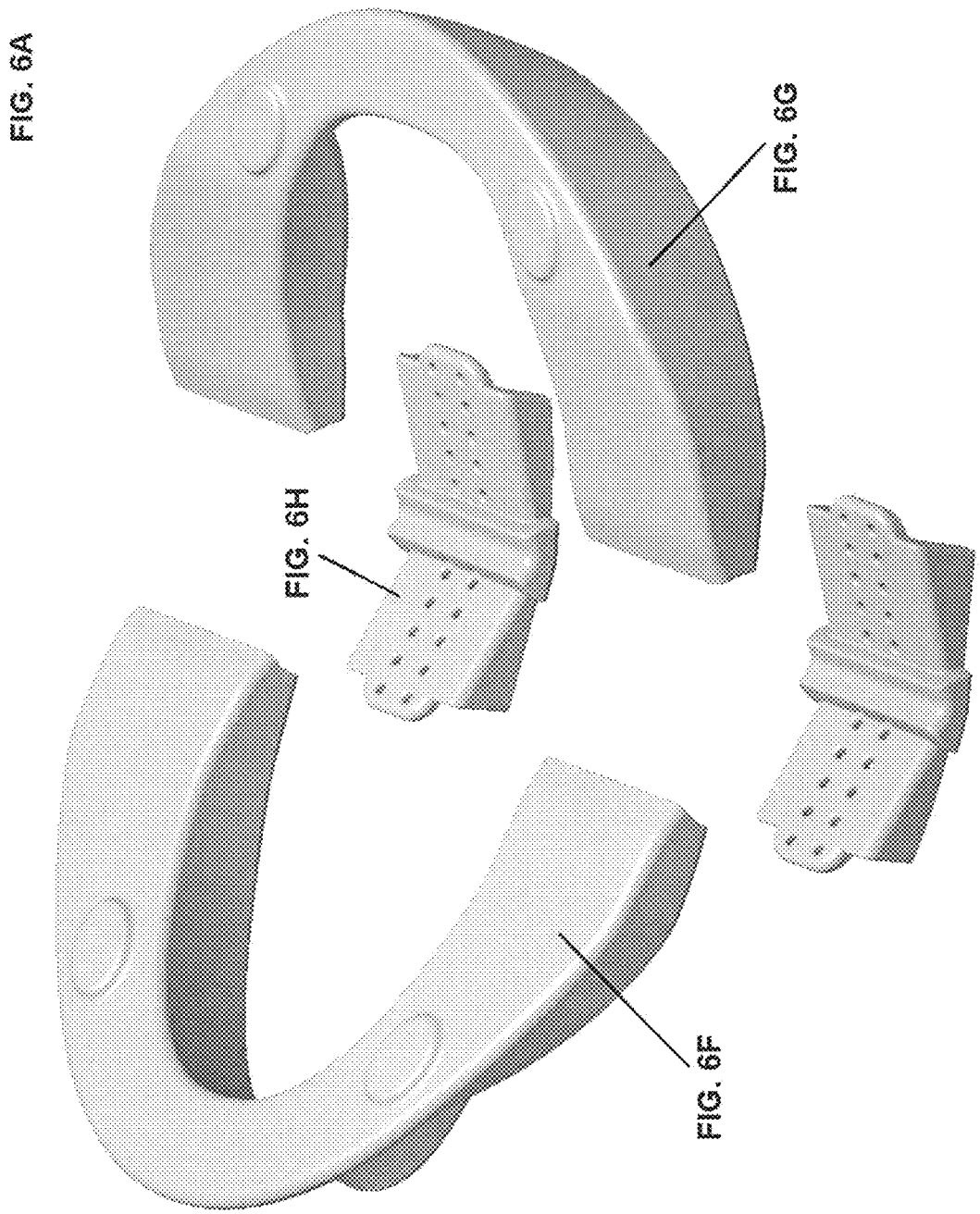

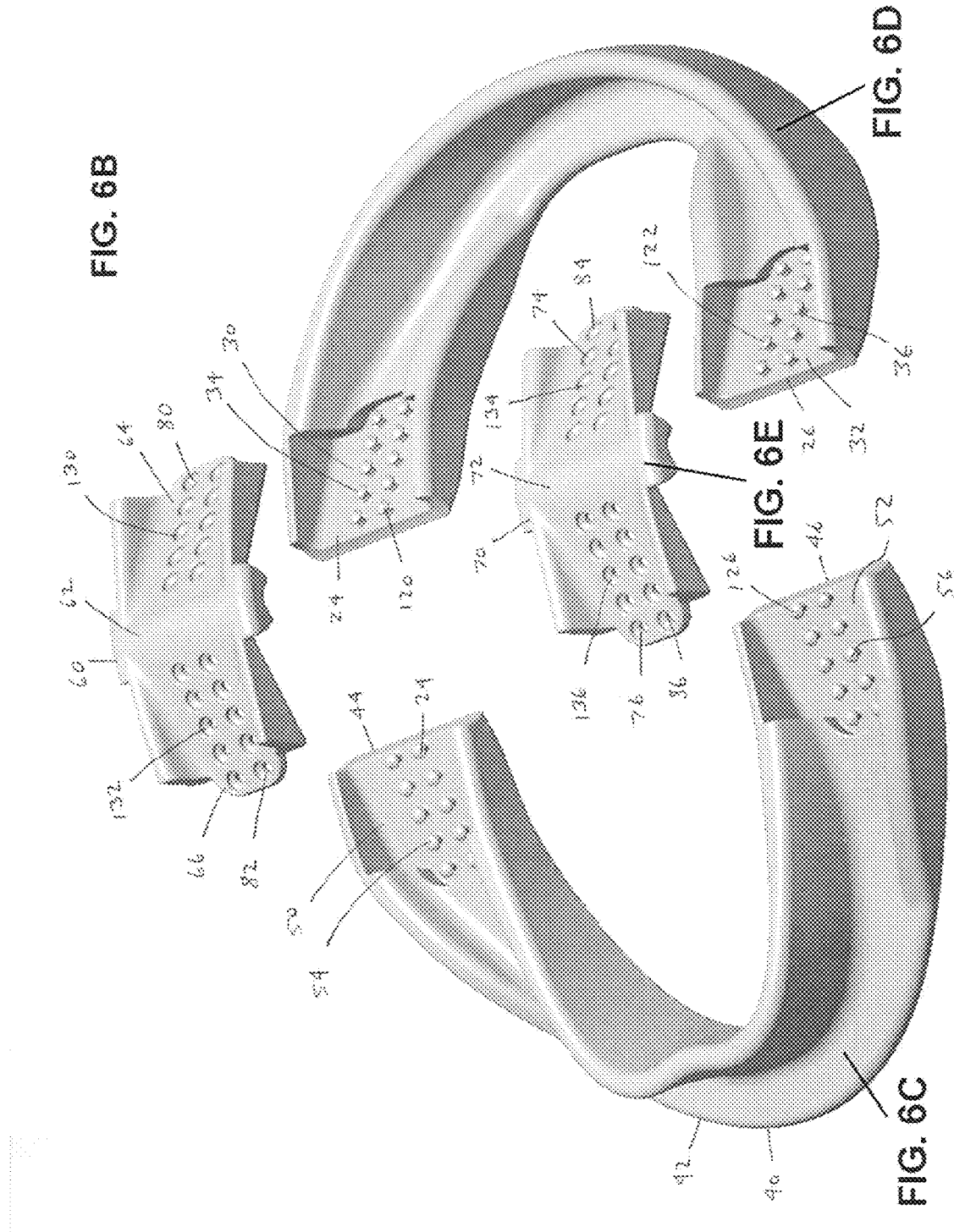

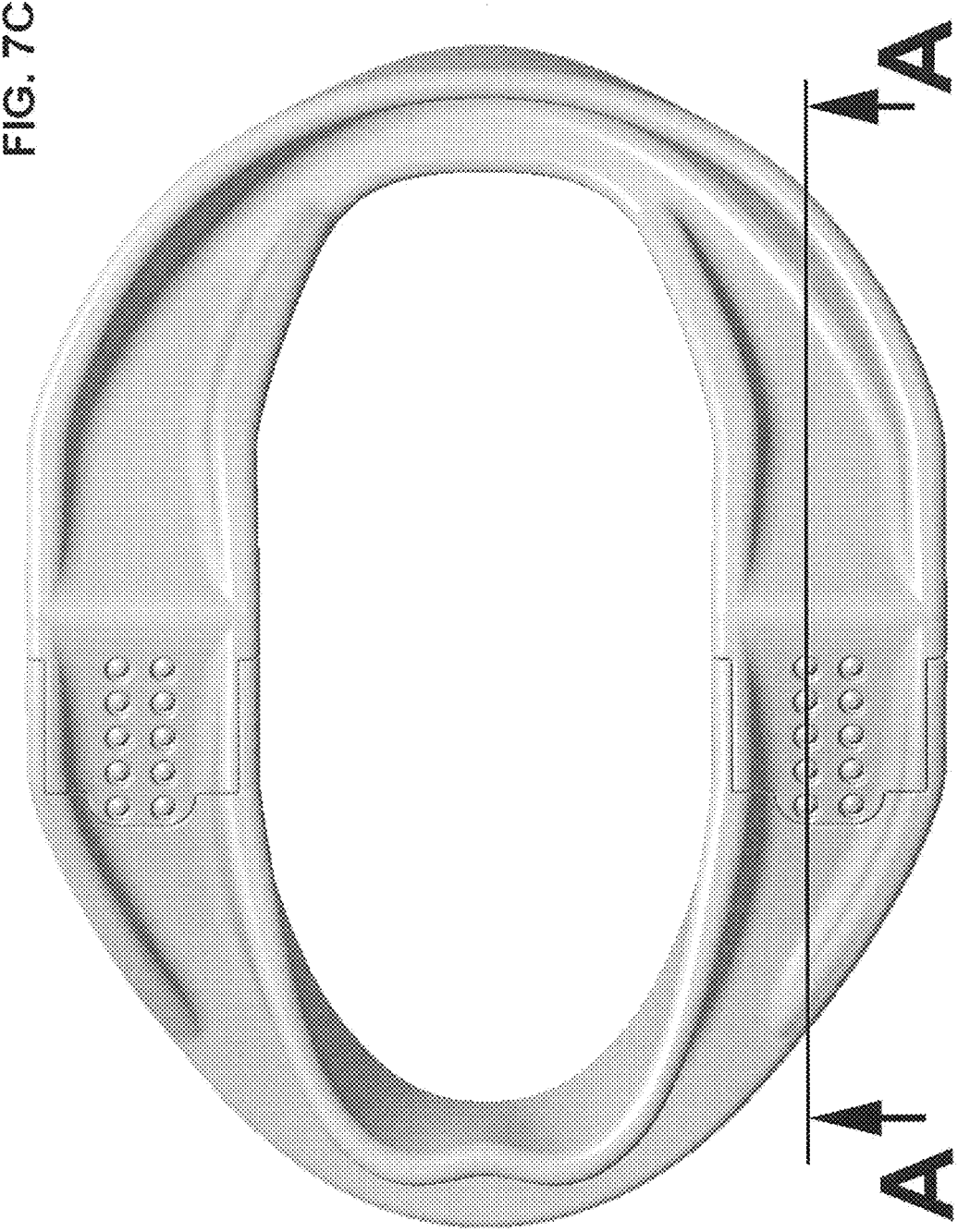

SECTION A-A

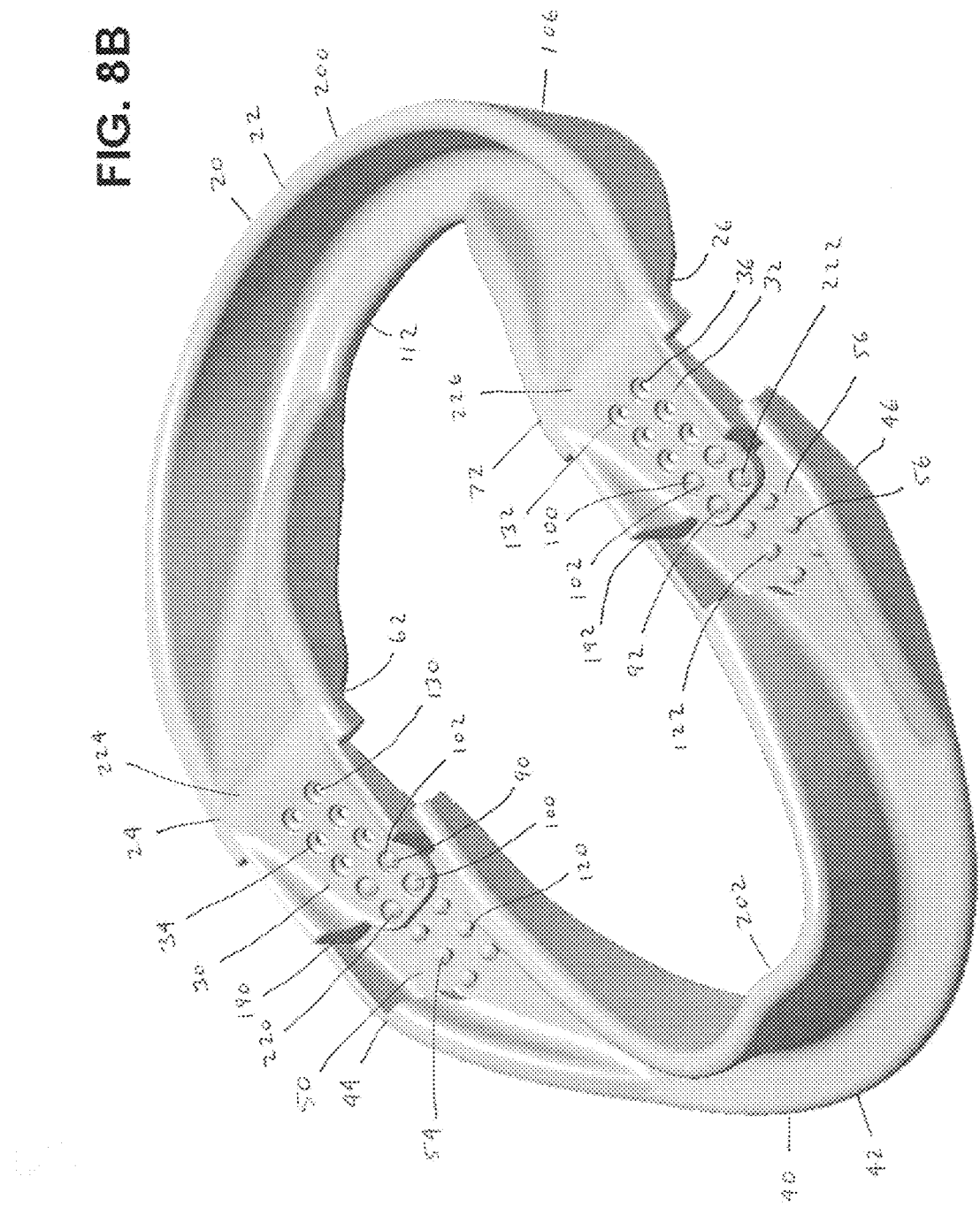

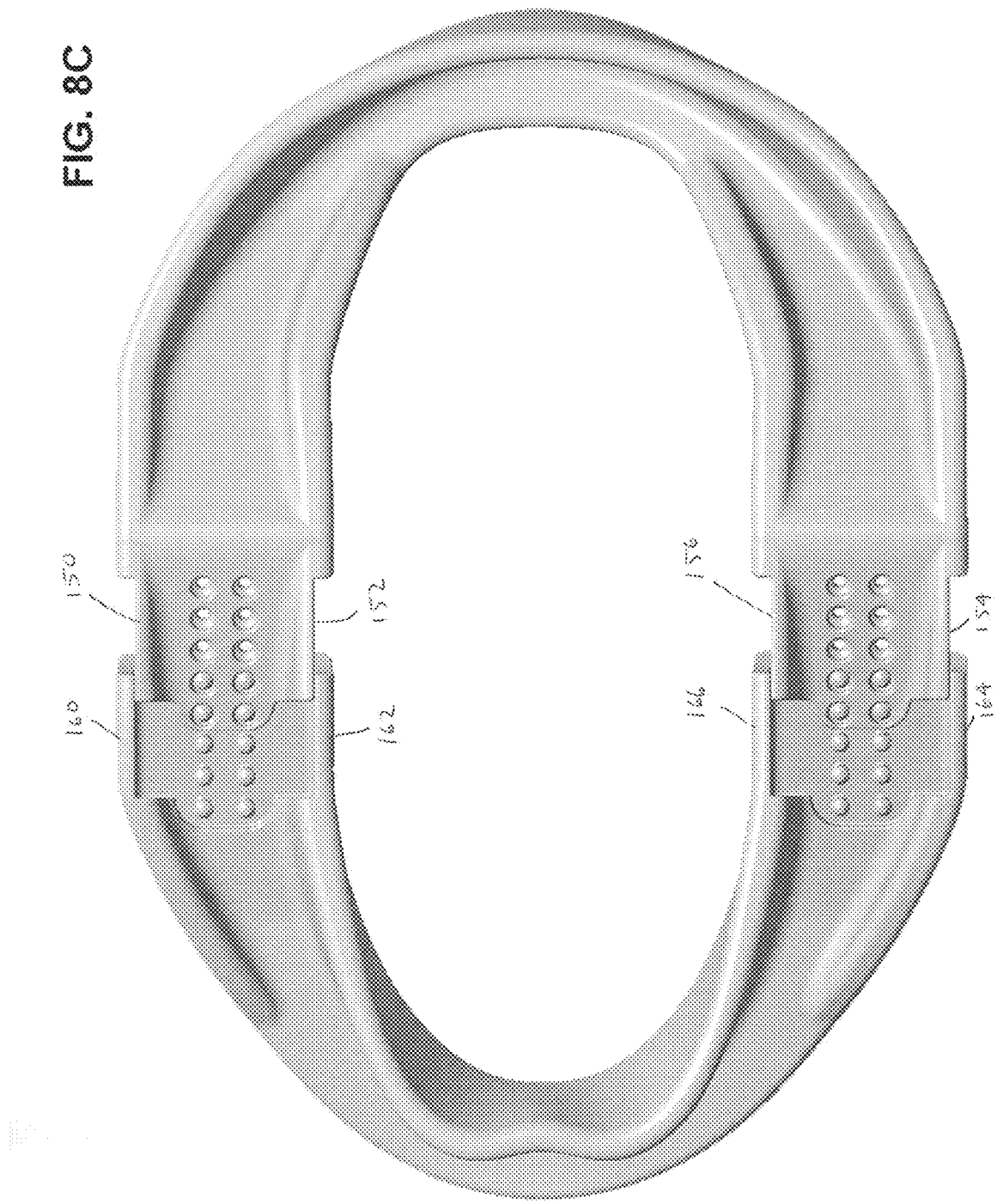

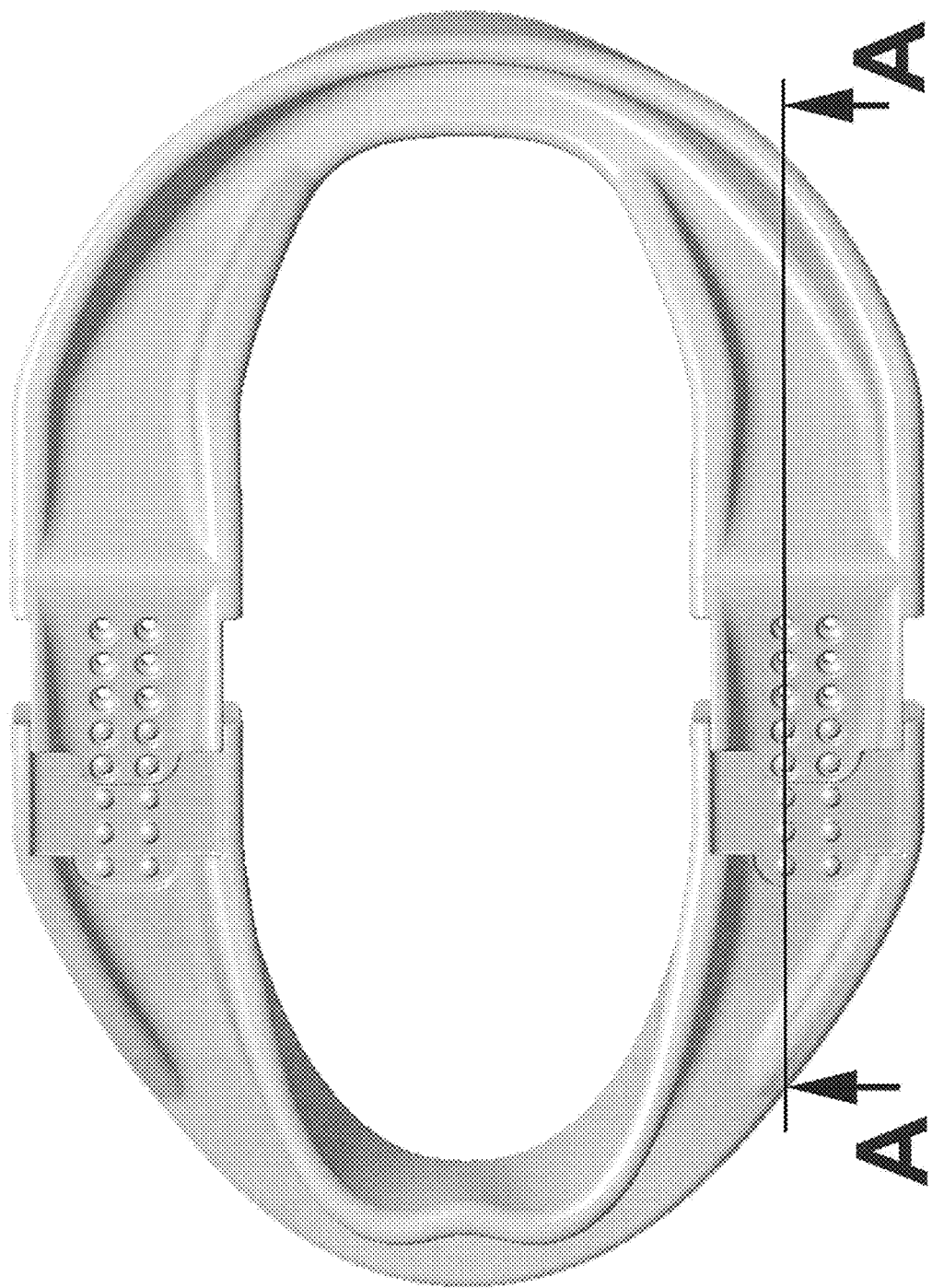

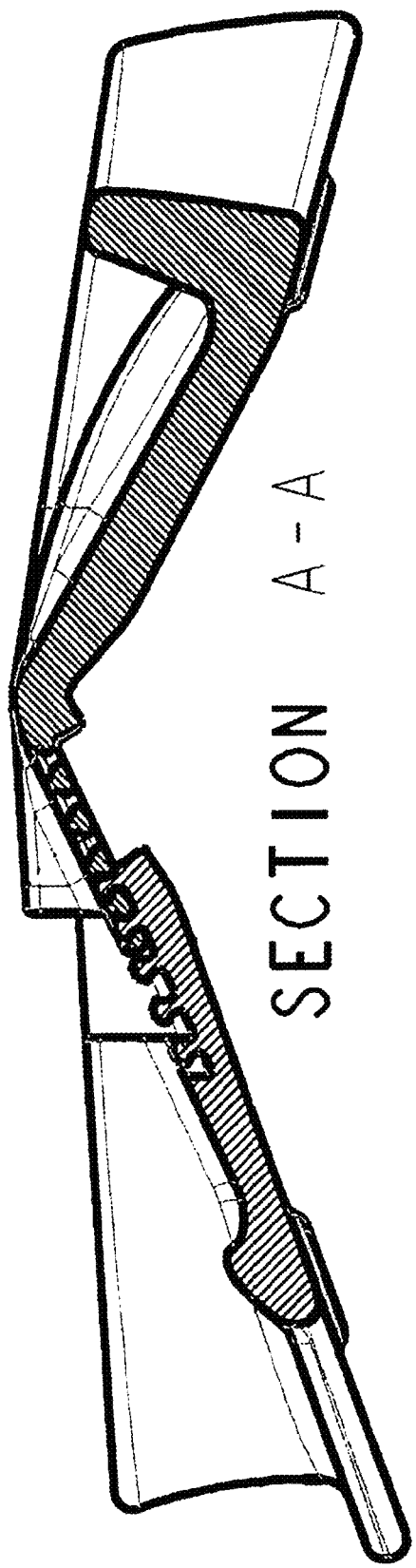

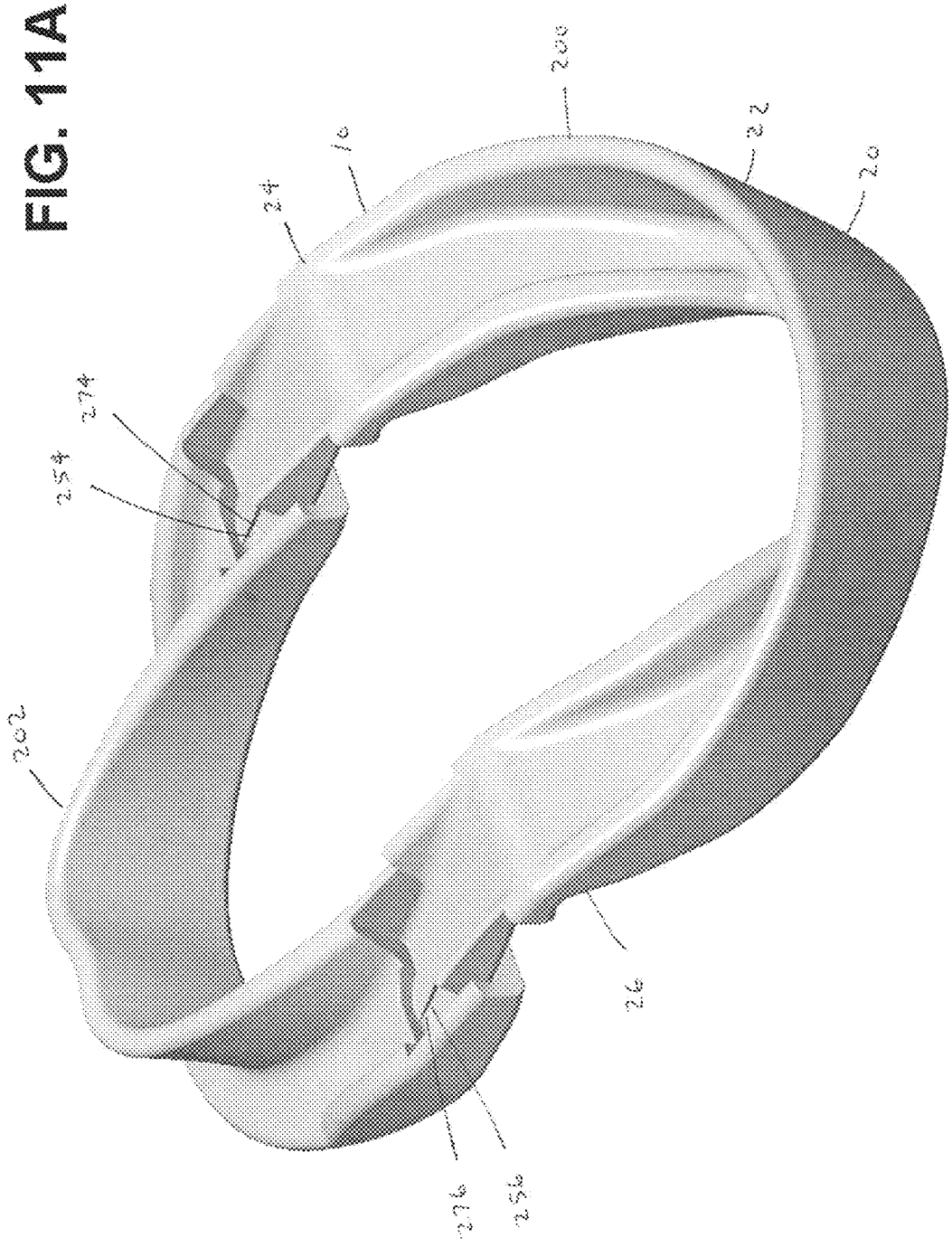

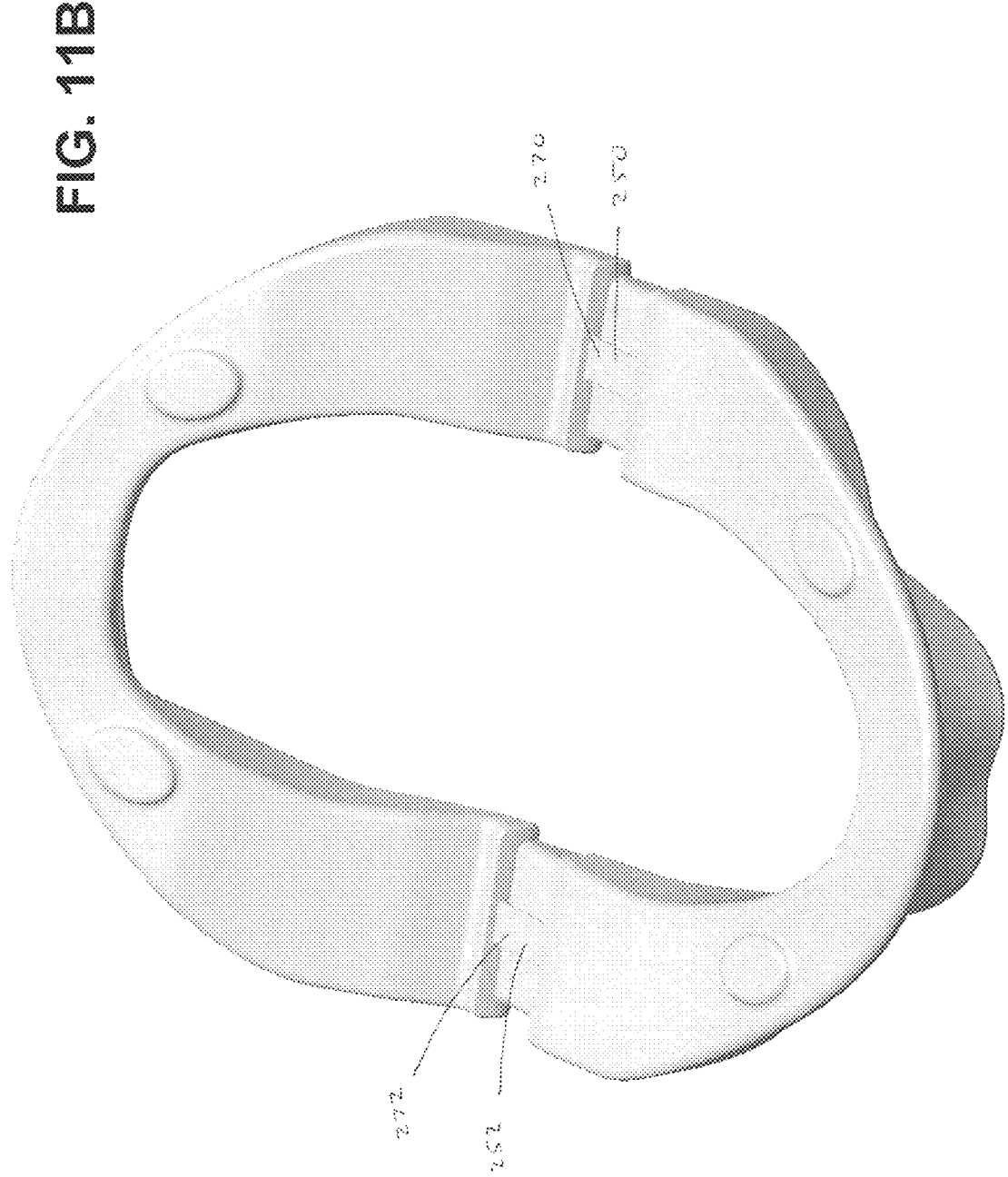

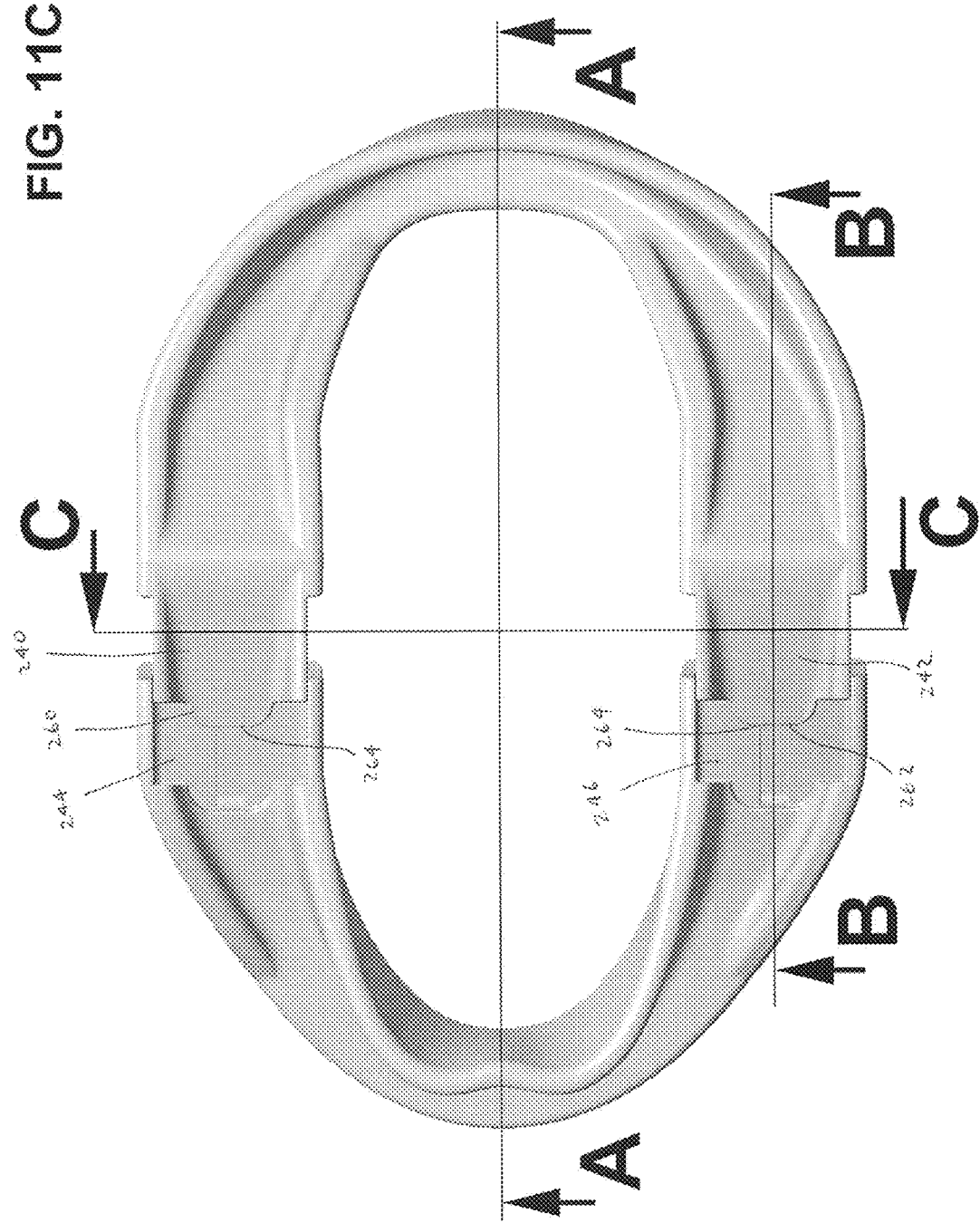

SECTION A-A

SECTION B-B

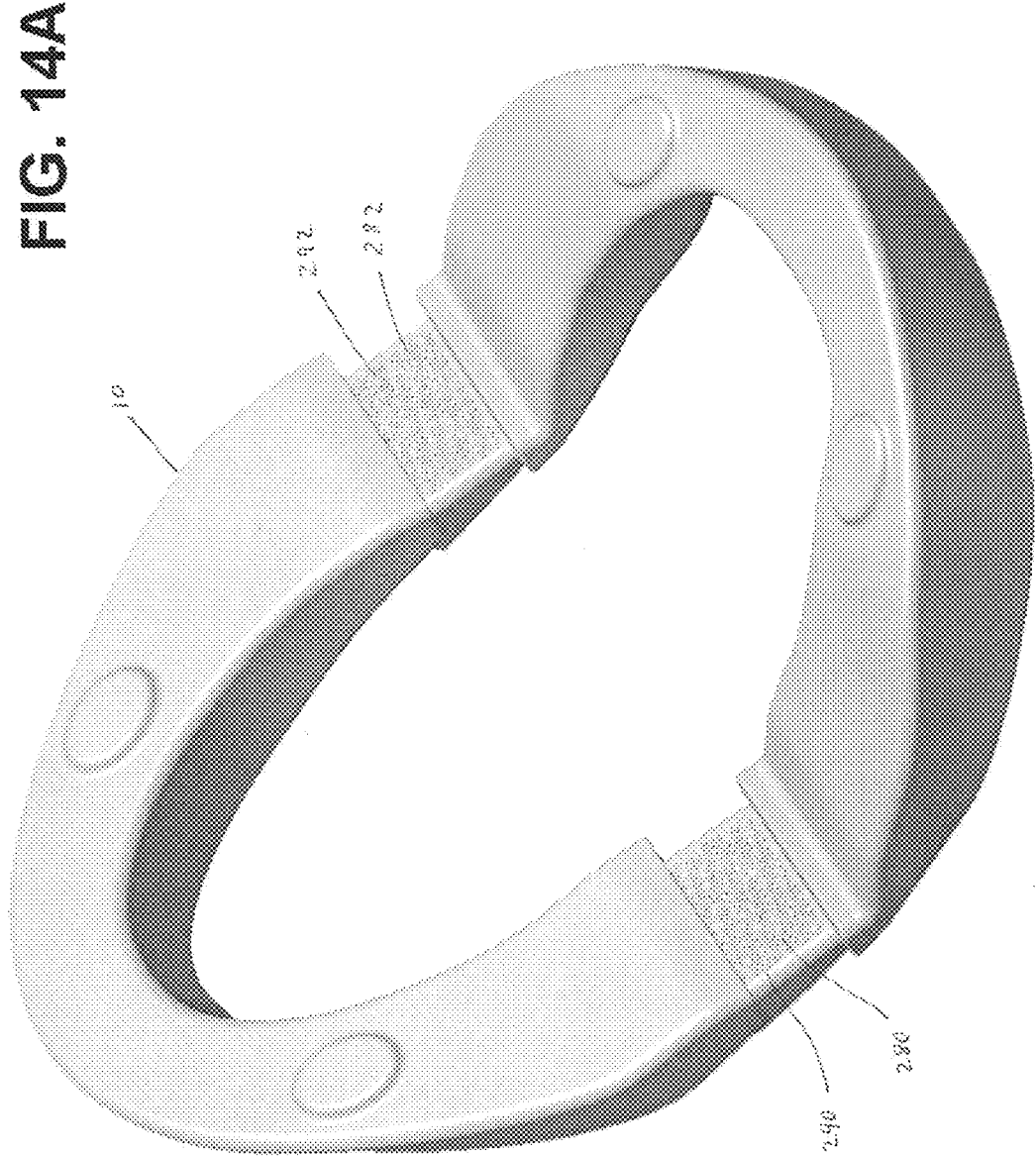

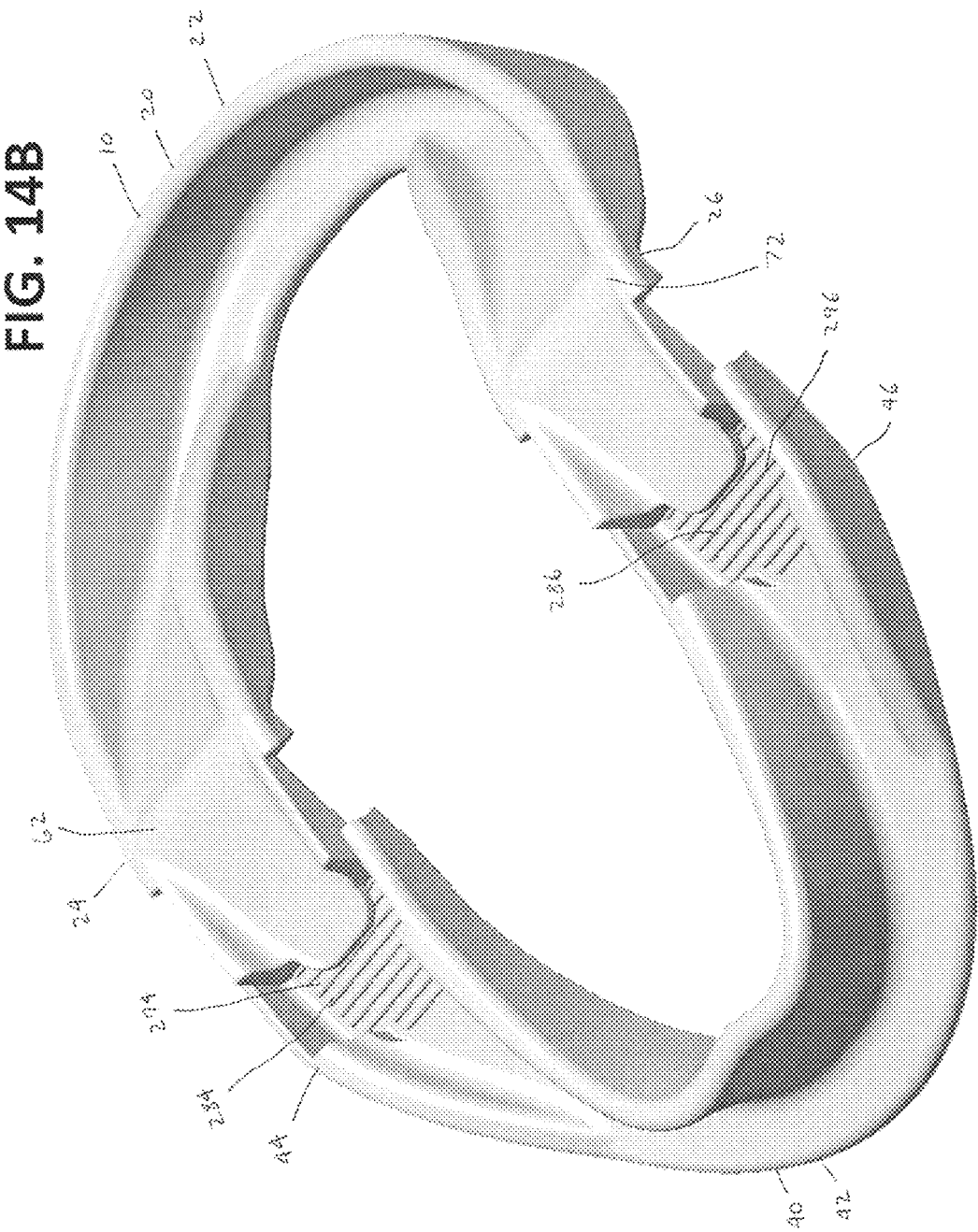

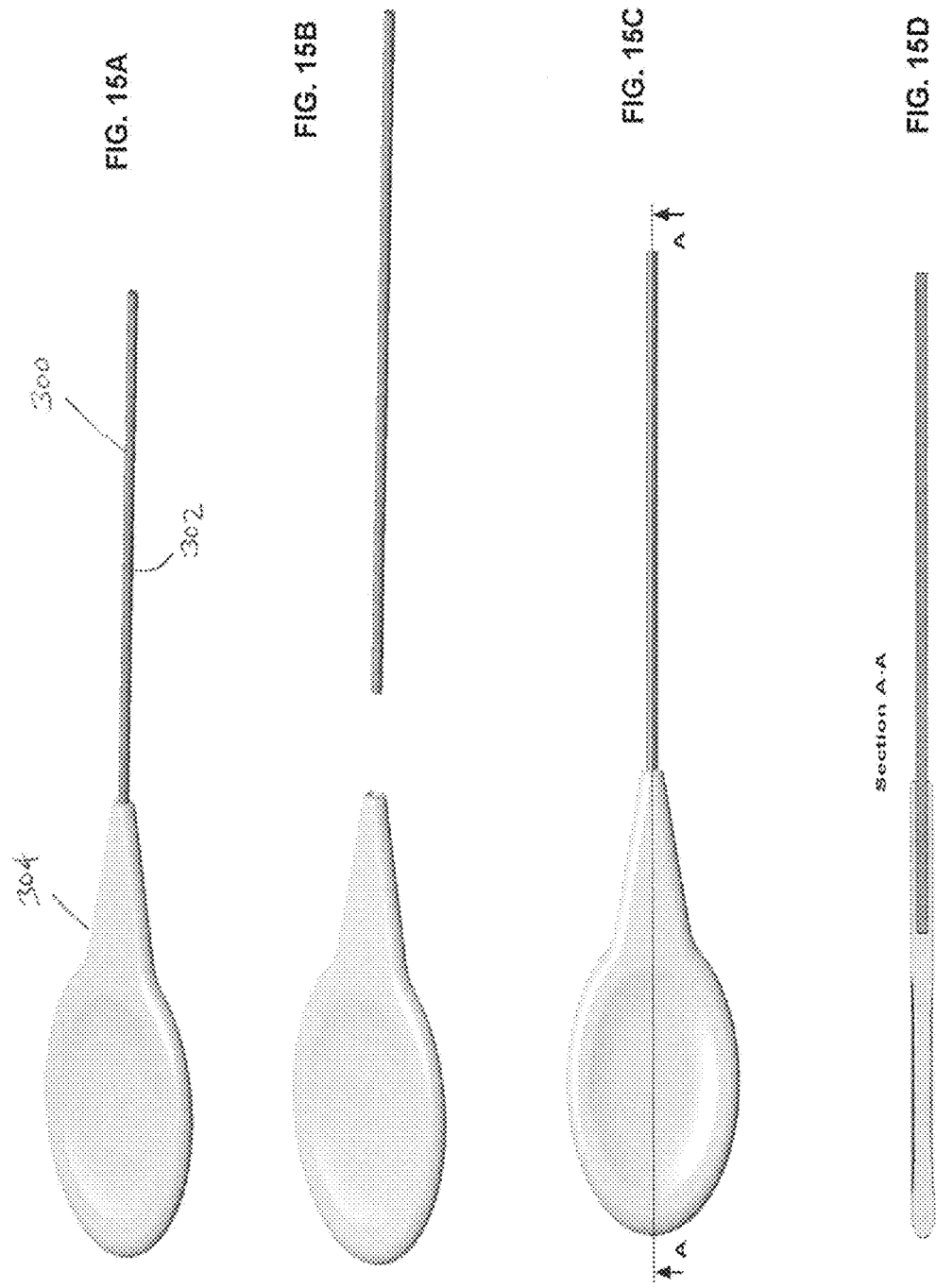

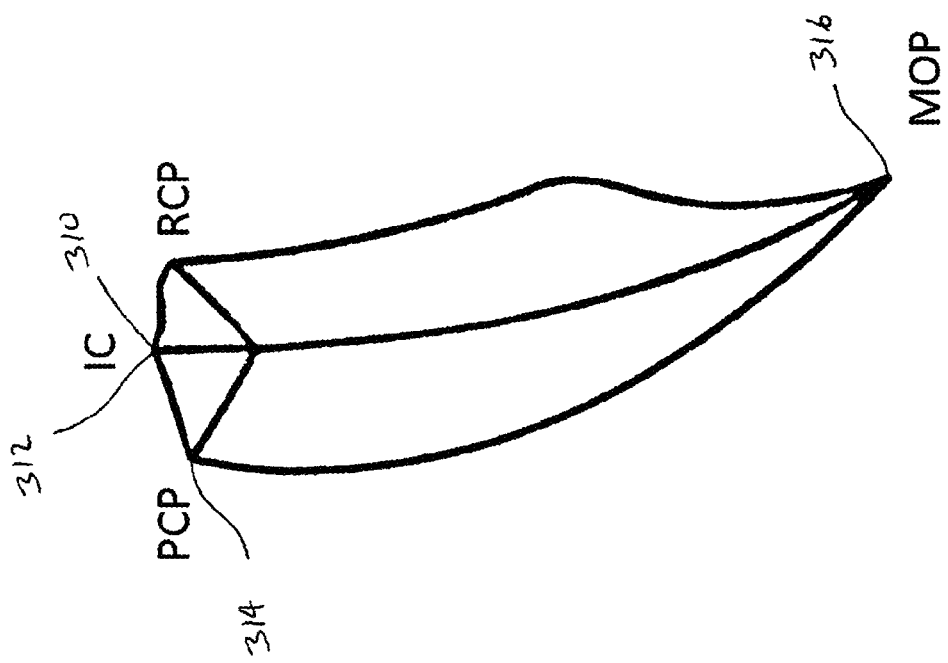

INCREMENTAL AND/OR SUCCESSIVE ADJUSTABLE MANDIBULAR ADVANCEMENT DEVICE FOR PREVENTING AND TREATMENT OF SNORING AND OBSTRUCTIVE SLEEP APNEA

FIELD OF INVENTION

The current invention relates to an adjustable mandibular advancement device which by virtue of either an incremental (stepwise) or a successive (continuous) mechanism, advances the mandibular relative to the maxilla in order to prevent or reduce Snoring and/or Obstructive Sleep Apnea Syndrome (OSAS) during sleep.

BACKGROUND OF THE INVENTION

Snoring and Obstructive Sleep Apnea are generally known today as the same disease on a continuum of the sleep disorder severity scale. Starting at the modest degree of snoring ending in the fulminate obstructive sleep apnea condition, is known as a fact.

As the disease is closely related to a large variety of physical and mental conditions, treatment is of outmost importance as soon as possible.

Whereas the snoring condition is characterized by the sounds developed by vibrating tissues in the most dorsal area of the pharynx, either the nasopharynx, or the oropharynx or the laryngopharynx, the obstructive sleep apnea is characterized by actual respiration arrest caused by occlusion of the pharyngeal airways.

Apnea appears when the upper airway passages are being sucked close to the rear part of the throat when the person is trying to breathe during sleep. The occlusion can be the result of suction or by the lapse of tonus in the oral soft tissues during the relaxed sleep condition.

When the occlusion is there, no air is passing through the pharynx and down to the lungs this is the situation called OSAS (Obstructive Sleep Apnea Syndrome).

The obstruction can happen as often as 1000 times during the night time sleep in which the body is depraved from oxygen uptake from the air into the blood stream, which eventually leads to the aggravated symptoms.

The severity of OSAS has been described in the medical literature numerous times giving cause to a number of symptoms and diseases:
General headache
High blood pressure
Diabetes
Hypoxic pulmonary vasoconstriction
Cardiomyopathy
Pulmonary hypertonia with cor pulmonale (increased pressure in the heart-lung circuits)
Heart failure, heart arrhythmia, heart attack
Day time melancholy or depression
Intelligence alterations
Acid Reflux (GERD—Gastro Esophageal Reflux Disease)
Potency disturbances
Worsening of ADHD (Attention deficit hyperactivity disorder), in addition to a large number of problems of a more social character, like, e.g., divorce, decreased labour activity, difficulties in keeping conversations in the track due to tiredness, etc.

Thus, compared to a normal control group without diseases, patients suffering from snoring and/or OSAS appear to have three times as many cases of coronary heart diseases, four times as many cerebral illnesses, such as clots, twelve times as many incidents of car accidents and twice as many labour accidents due to day time sleepiness as a result of lack of sleep and/or impaired sleep quality.

Due to these conditions the life time expectancy is severely limited for these patients, and their quality of life is compromised.

The continuum of snoring diseases gives the following frequency figures;
40% of adults over 40 snore (approx. 87 million Americans)
9% of men and 4% of women suffer from some form of OSAS
(approx. 30 million Americans)
Less than 10% of OSA sufferers have been diagnosed
(Approx 3 million Americans)
Of those, less than 25% have been successfully treated.

For the above reasons, it is important to provide devices to eliminate and prevent apnea and the incipient stages thereof.

In the prior an, a number of surgical techniques for removal of the tissue involved in the obstruction have been developed, but all of these techniques seem to incur a certain invalidation of the patient and, at the same time, do not have a fully predictable effect.

Furthermore, a number of medical treatments have been tried out with predominantly deficient or sometimes even damaging effect.

Finally, the scientific literature and the patent literature disclose numerous devices for alarming the snoring patient during sleep; devices for tongue thrust, devices for forward movement of the soft palate; devices for obstructing the oral cavity (delimited by the lips), thereby engaging the sound from the snoring; furthermore, mandibular advancement splints or appliances, mouth guard-like devices for provocation of either tongue, hyoid bone or jaw position changes, thereby eliminating snoring;—all of these requiring active participation from competent professionals, such as medical doctors, dentists, etc. Among such prior art devices for or attempts to inhibit snoring, the following are of particular interest in the present context.

EP 0 794 749 B1 discloses a jaw position-regulating oral device for preventing snoring and obstructive sleep apnea during sleep. The device consist of two members, a first member to engage with the maxillary dentition and a second member to engage with the mandibular dentition, both connected by a resilient hinge. The mechanism is embedded in the mandibular advancement relative to the maxilla.

WO 2013/032 884 A1 discloses a mandibular advancement device with an upper and lower member to engage the maxillary and mandibulary dentition respectively. The lower tray assembly is mated to and slidably adjustable by the patient relative to the upper tray assembly.

WO 2009/062 541 A1 discloses a mandibular advancement orthosis in which the device the comprises a unitary flexible member that can be folded on itself for interaction with the teeth of the upper and lower arches, and an interchangeable flexible strip for surrounding the teeth of the upper arch, having a length that can be modified in order to obtain the desired level of mandibular advancement.

US 2009/0014 013 A1 discloses a mandibular advancement splint made of two thermoformable trays designed to envelop the upper and lower arch. The advancement splint includes an articulated frame having rigid and flexible elements immersed in the thermoformable flexible material or molded around it.

EP 1 719 481 A1 discloses a mandibular advancement device with a lateral link incorporated into a mandibular protrusion device comprising an upper dental tray and a lower dental tray so as to advance or retract the lower dental arch during a vertical movement between the two. The link is adapted to be detachably accommodated in an opening of a ball pivot.

EP 2 529 710 A1 discloses a device for mandibular advancement in which an upper member and a lower member are interconnected by means of pivotable connection in which at least one is formed as a stud.

CA 223 650 3 A1 discloses a mandibular advancement device which uses elastic bands to pull the jaw forward. The upper part having a set of retention hooks and the lower part having a set of interchangeable slide-in posterior occlusal bite planes.

WO 2008/130 413 A1 discloses a mandibular advancement device for pulling the lower jaw forward composed of an upper and a lower member to engage the dentition, where a ball type of hook support is located on both sides of the upper tray at a forward position and a ball type of hook supports are located at a rearward position of both sides of the lower jaw. A tension coil is attached to each of the upper and lower ball type of hook supports.

WO 2011/115 962 A1 discloses a mandibular advancement splint made of two trays designed to envelop the upper and lower arch. The upper appliance has a pair of adjustable wings attached to the body, and the lower has a pair of fixed wings attached to the body. The upper wings are slidable adjustable.

US 2010/004 380 5 A1 discloses a mandibular advancement device with an upper and lower member to engage with the dentition of the human. The lower dental plate having two pairs of spaced apart pillars and two removable attachable horizontal displacements inserts on the upper part.

GB 2 264 868 discloses an anti-snoring device for oral use, comprising members having upper and lower surfaces which engage the user's maxillary and mandibular dental arches respectively. The upper and lower surfaces are spaced so that the mandible is placed in a forwardly offset position relative to its normal position. The spacing also tensions the masticatory muscles to maintain the device in place.

US 2011/001 722 0 A1 discloses a self-titratable mandibular repositioning device that allows for adjusting the maintained forward position by simply biting-down to preserve the desired degree of mandibular advancement, made of a lower and an upper member to engage the dentition.

US 2008/011 579 1 A1 discloses a mandibular advancement device with an intraocclusal removable device in the form of a "U" that is placed covering the all of the upper jaw teeth, wherein two steps, one in each extreme of the lower part of the element, which impede the mandible be closed completely on its normal occlusion, forcing it to produce a forward displacement of the lower jaw.

US 2005/023 600 3 A1 discloses a mandibular advancement device as a single piece of molded plastic with said unit modeled from four theoretical positions including a shield like anterior portion fitted and anchored between anterior teeth-gums and behind the lips.

US 2010/030 045 8 A1 discloses a mandibular advancement device with an upper and lower member to engage with the dentition of the human. The members are including a cam associated with one of the jaws and a follower associated with the other jaw.

US 2008/009 902 9 A1 discloses a mandibular advancement device composed of a maxillary main body for removable attachment to the maxillary teeth with a protrusive element extending from the central portion of the body and a mandibular removable appliance attached to the mandibular anterior teeth.

EP 2 491 901 A1 discloses regulatable intraoral mandibular advancement device for preventing snoring and sleep apnea in which a screw system is located in the central part of the connection between the upper and lower members for the engagement of the dentition.

AU 1999 476 15 B2 discloses a mandibular advancement device in which the upper jaw is firmly fitted into an upper plate and the lower jaw is firmly fitted into a lower plate, these two parts are connected by means of opposing flange components located to be lying in an area and close to the posterior teeth.

US 2013/001 476 5 A1 discloses a tongue and mandibular advancement device in which an upper member has hook supports anteriorly and a lower member has a plurality of hook support at the rearward position.

EP 0 337 201 discloses an orthodontic appliance comprising a first member to engage with the mandibular dentition and a second member to engage with the maxillary dentition. The two members are resiliently hinged together to keep the upper and lower jaw in a normal position.

WO 92/11827 discloses an anti-snoring device for oral use consisting of a horseshoe-like upper jaw member for engaging the maxillary dentition, with the downward extending flange intended to extend into the lingual vestibule in order to maintain a forward posture of the lower jaw.

EP 0 312 368 discloses an anti-snoring device for oral use which resembles the above-mentioned device, the main difference being, the design of the airway passage.

WO 92/05752 discloses an anti-snoring device for oral use consisting of a spatial member congruent with the palate and a lower member adapted to the lingual aspects of the surfaces of the dentition in the lower jaw, hooks being attached to the occlusive plane of the device for fixing the two jaws in a predetermined relation.

U.S. Pat. No. 5,313,960 discloses an anti-snoring device for oral use consisting of two horseshoe-like individually shaped mouthpiece portions which are connected and fixed in a predetermined position in which the lower jaw protrudes in relation to the upper jaw.

While the above devices represent attempts to solve the snoring and apnea problems, they are all rather complicated in their design and most of these require the interaction of a professional team in their individual design. Furthermore, they are rather discomfortable for the wearer, and they do not appear convincing with respect to their capability of achieving an effective and long-tasting anti-snoring effect.

Thus, there is a demand for a relatively comfortable device which provides a high degree of inhibitory effect on snoring during even long sleeping periods, such as overnight, without adverse effects on the structures involved, and which at the same time is easy and simple to use and wear for normal non-skilled persons. The present invention provides such a device.

SUMMARY OF THE INVENTION

The present invention is defined by the appended claims with specific embodiments being shown in the attached drawings. For the purpose of summarizing the invention, the invention relates to an incremental mandibular advancement anti-snoring and obstructive sleep apnea preventing device for a human. The adjustable anti-snore device according to the invention comprises an upper member adapted to engage the maxillary dentition of a human and a lower member adapted to engage the mandibulary dentition of the human, the upper and lower members being resiliently or mechanically hinged together, wherein the resiliency of the hinging is adapted to allow the physiological movement of the lower jaw in the sagital plane while retaining a forward position of the lower jaw relative to the upper jaw and thereby keeping the airway passage in the nasopharynx, the oropharynx and the hypopharynx substantially free of occlusion, while at the same time embody the adjustability in one or two form, i.e. incremental and/or successive.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention, it should be appreciated by those skilled, in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 1A shows the incremental version of the adjustable mandibular advancement device top view in an oblique perspective in its neutral position;

FIG. 1B shows the incremental version of the adjustable mandibular advancement device bottom view in an oblique perspective in its neutral position;

FIG. 2A shows the incremental version of the adjustable mandibular advancement device from aside in its neutral position;

FIG. 2B shows the incremental version of the adjustable mandibular advancement device in sectional view along line A-A in FIG. 1C in its neutral position;

FIG. 2C shows the incremental version of the adjustable mandibular advancement device in sectional view along line B-B in FIG. 1C in its neutral position;

FIG. 4D shows the incremental version of the adjustable mandibular advancement device top view in a perpendicular perspective in its maximal elongated position;

FIG. 5B shows the incremental version of the adjustable mandibular advancement device in sectional view along line A-A in FIG. 4C in its maximal elongated position;

FIG. 5C shows the incremental version of the adjustable mandibular advancement device in sectional view along line B-B in FIG. 4C in its maximal elongated position;

FIG. 6A shows the incremental version of the adjustable mandibular advancement device in its four components top view oblique perspective;

FIG. 6B shows the incremental version of the adjustable mandibular advancement device in its four components bottom view oblique perspective;

FIG. 6C shows the mandibular lower member to engage with the mandibular dentition of the incremental version of the adjustable mandibular advancement device bottom view oblique perspective;

FIG. 6D shows the maxillary upper member to engage with the maxillary dentition of the incremental version of the adjustable mandibular advancement device bottom view oblique perspective;

FIG. 6E shows the hinge mechanism connecting the upper maxillary and lower mandibulary members of the adjustable mandibular advancement Device in a bottom oblique view;

FIG. 6F shows the mandibulary lower member to engage with the maxillary dentition of the incremental version of the adjustable mandibular advancement device top oblique view;

FIG. 6G shows the maxillary upper member to engage with the mandibular dentition of the incremental version of the adjustable mandibular advancement device top oblique view;

FIG. 6H shows the hinge mechanism connecting the upper maxillary and lower mandibulary members of the incremental version of the adjustable mandibular advancement device in a top oblique view;

FIG. 7C shows the single member adjustable incremental version of the adjustable mandibular advancement device bottom view in a perpendicular perspective in its neutral position;

FIG. 8B shows the single member adjustable incremental version of the adjustable mandibular advancement device bottom view in an oblique perspective in its maximal elongated position;

FIG. 8C shows the single member adjustable incremental version of the adjustable mandibular advancement device bottom view in a perpendicular perspective in its maximal elongated position;

FIG. 8D shows the single member adjustable incremental version of the adjustable mandibular advancement device bottom view in a perpendicular perspective in its maximal elongated position;

FIG. 8E shows enlarged schematic details in sectional view along line A-A in FIG. 8D of the incremental mechanism with taps and corresponding holes in just one of the members in its maximal enlarged position;

FIG. 11A shows the successive version of the mandibular advancement device in which a sliding, system is indicated and where the sliding system is in the form of a "dovetail guide structure" and is seen from an oblique perspective from the bottom part;

FIG. 11B shows the successive version of the mandibular advancement device in an oblique perspective from the top part, in which a sliding system is indicated;

FIG. 11C shows the successive version of the mandibular advancement device in a perpendicular perspective, in which a sliding system is indicated with its maximum elongation;

FIG. 14A shows the successive version of the adjustable mandibular advancement device top view in a oblique perspective in its maximum elongated position with visible platforms for the engagement of one part of the hook and loop system and noting that the platform can also be used as one part of a gluing surface;

FIG. 14B shows the successive version of the adjustable mandibular advancement device bottom view in its maximum elongated, position and noting that the platform connecting the two members can also be one part of a gluing surface;

FIG. 15A shows the heat applicable rod tool with it discoid handle and its pin in an oblique projection from above;

FIG. 15B shows the two parts of the heat applicable rod tool separated;

FIG. 15C shows the heat applicable rod tool with its handle and its pin from above;

FIG. 15D shows a sectional view along line A-A in FIG. 15C illustrating the heat applicable in which the embedded rod is enclosed by the handle material; and FIG. 16 shows a diagrammatic representation of the limitations of the movements of the lower jaw in any direction in the sagital plane where PCP stands for the most protruded contact point of the teeth, IC stands for intercuspidal position (the maximal closing point), RCP stands for the most retracted contact position for the teeth, and MOP stands for the maximal opening point.

DETAILED DISCUSSION

Figure 1C:
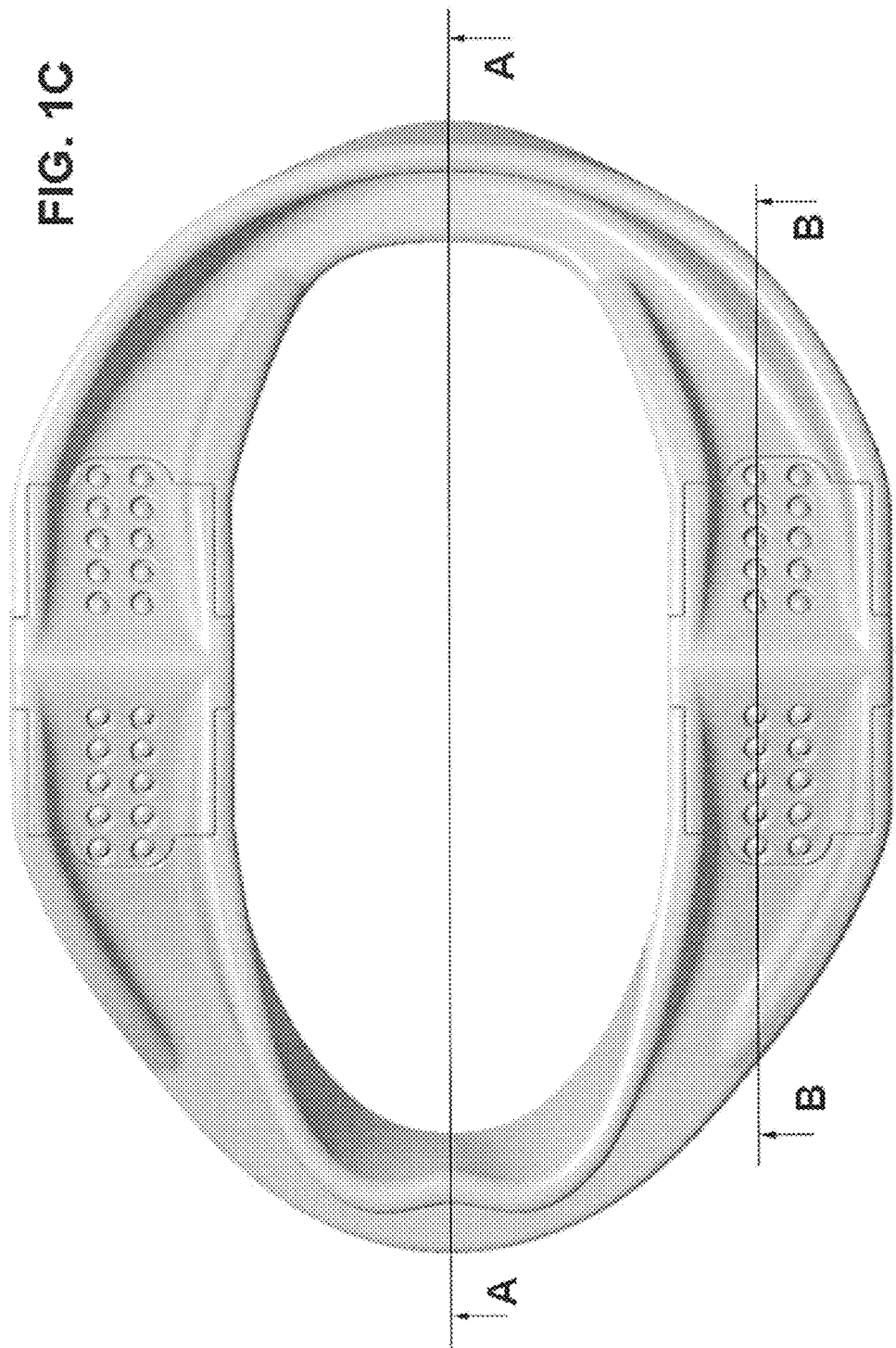
FIG. 1C shows the incremental version of the adjustable mandibular advancement device bottom view in a perpendicular perspective in its neutral position.
Figure 1D:
FIG. 1D shows the incremental version of the adjustable mandibular advancement device top view in a perpendicular perspective in its neutral position.
Figure 3:
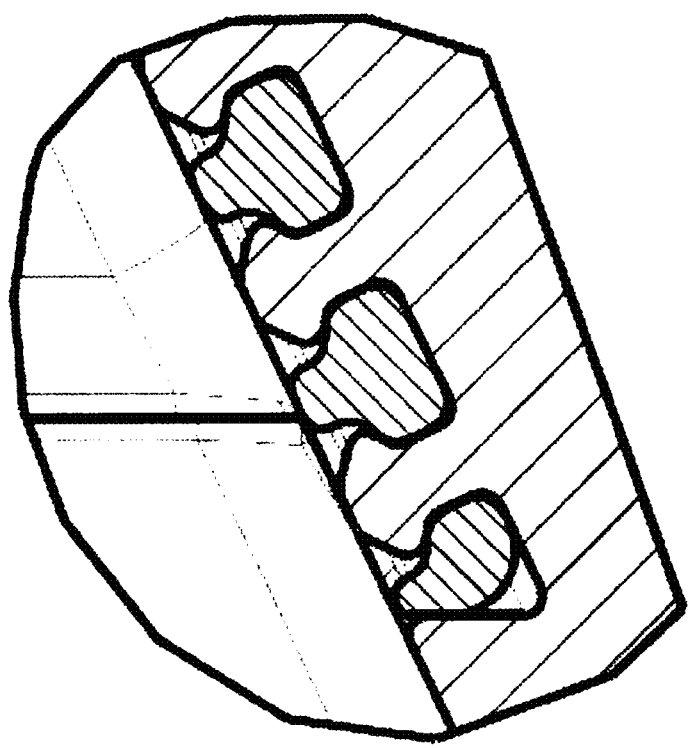
FIG. 3 shows enlarged schematic details of the incremental mechanism with taps and corresponding holes of FIG. 2C.
Figure 4A:
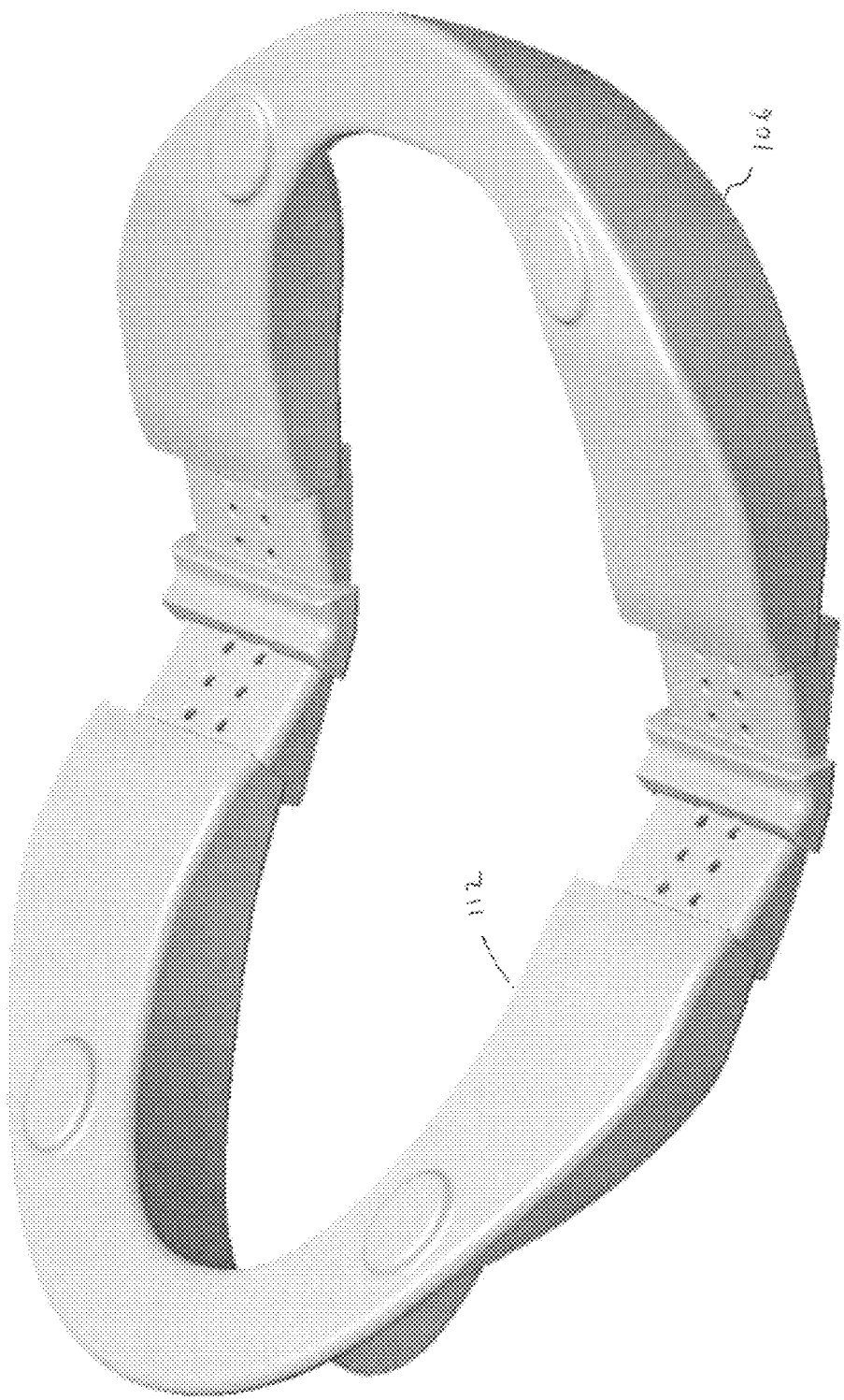
FIG. 4A shows the incremental version of the adjustable mandibular advancement device top view in an oblique perspective in its maximal elongated position.
Figure 4B:
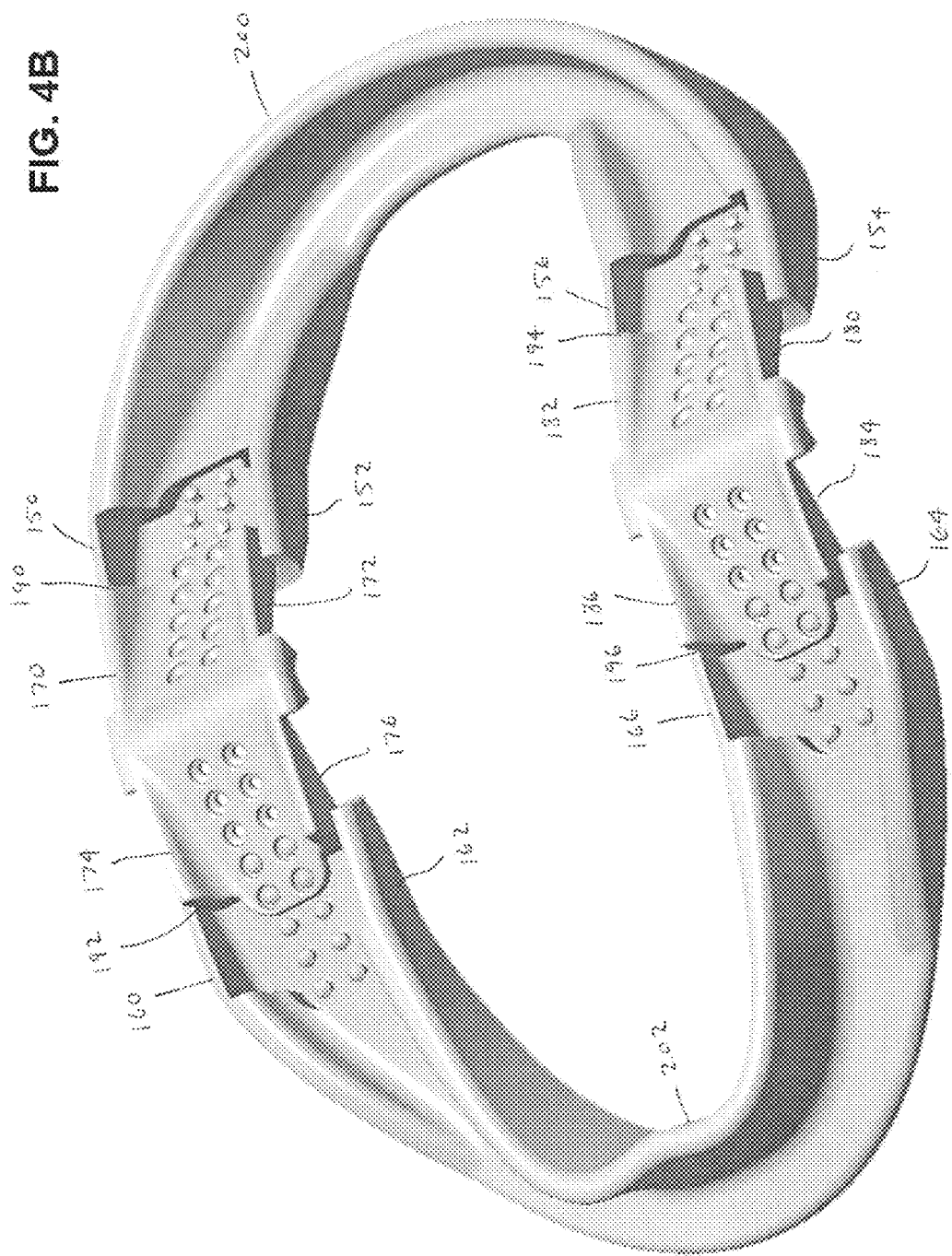
FIG. 4B shows the incremental version of the adjustable mandibular advancement device bottom view in an oblique perspective in its maximal elongated position.
Figure 4C:
FIG. 4C shows the incremental version of the adjustable mandibular advancement device bottom view in a perpendicular perspective in its maximal elongated position.
Figure 5A:
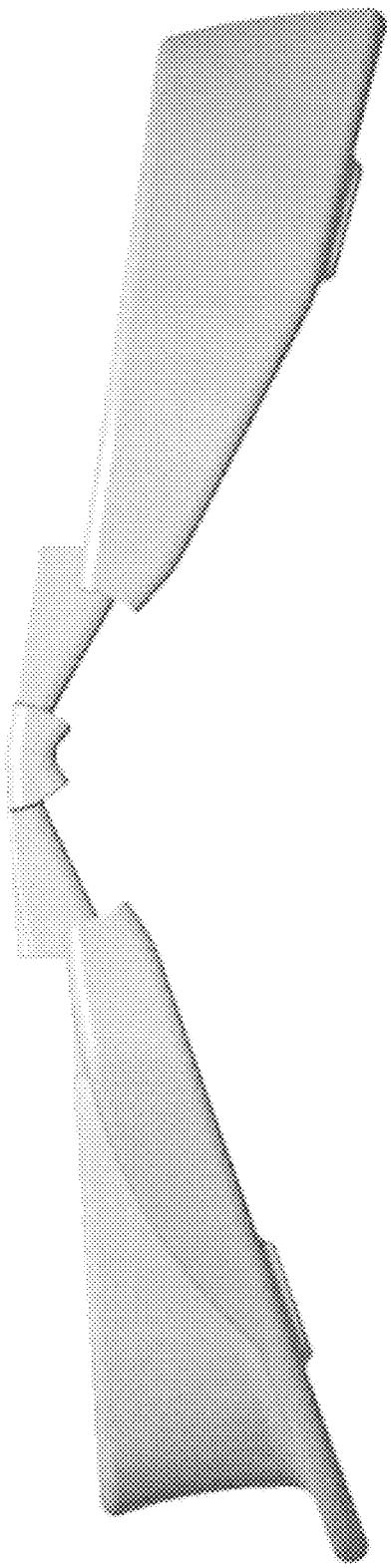
FIG. 5A shows the incremental version of the adjustable mandibular advancement device from aside in its maximal elongated position.
Figure 7A:
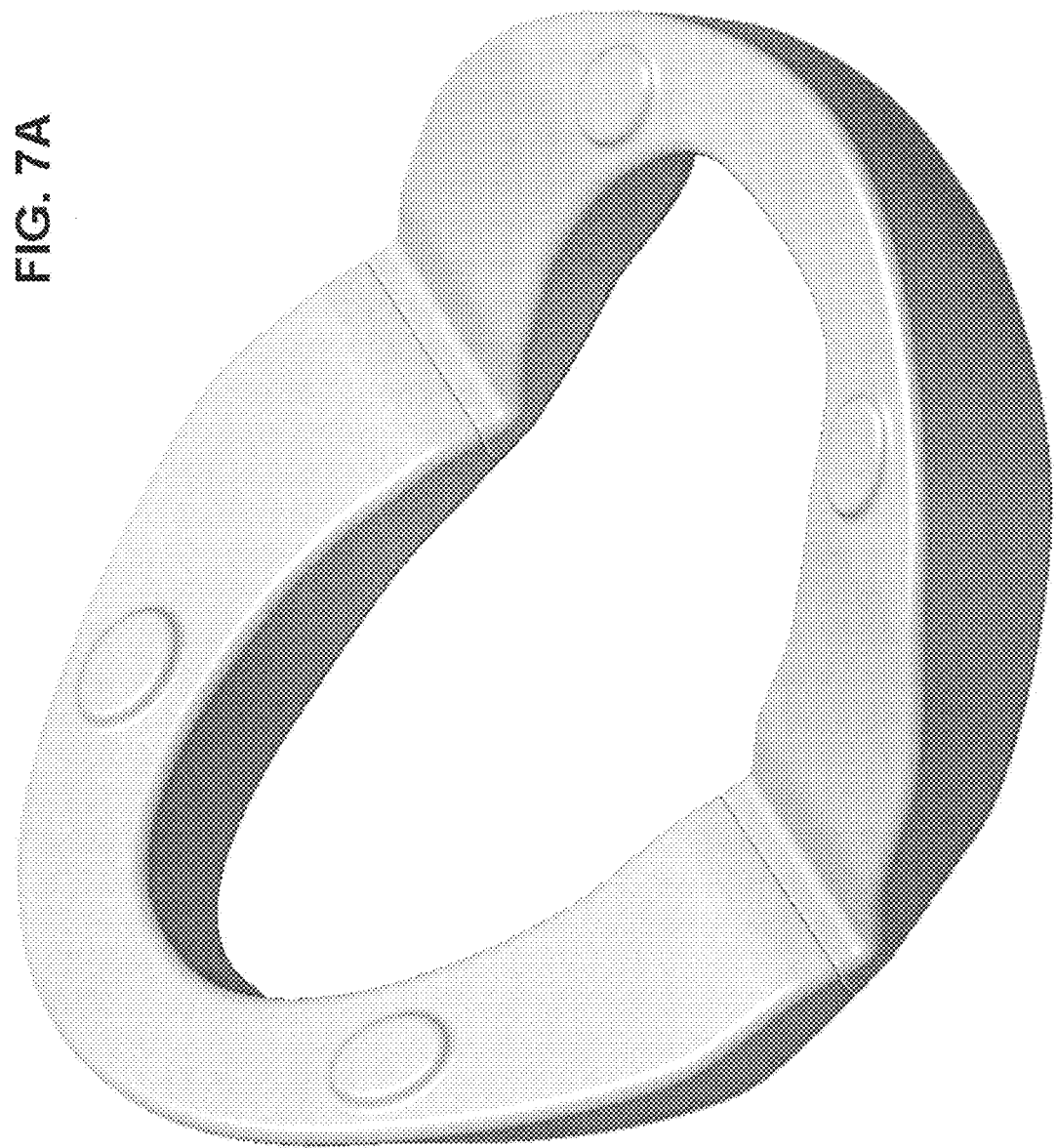
FIG. 7A shows the single member adjustable incremental version of the adjustable mandibular advancement device top view in an oblique perspective in its neutral position.
Figure 7B:
FIG. 7B shows the single member adjustable incremental version of the adjustable mandibular advancement device bottom view in an oblique perspective in its neutral position.
Figure 7D:
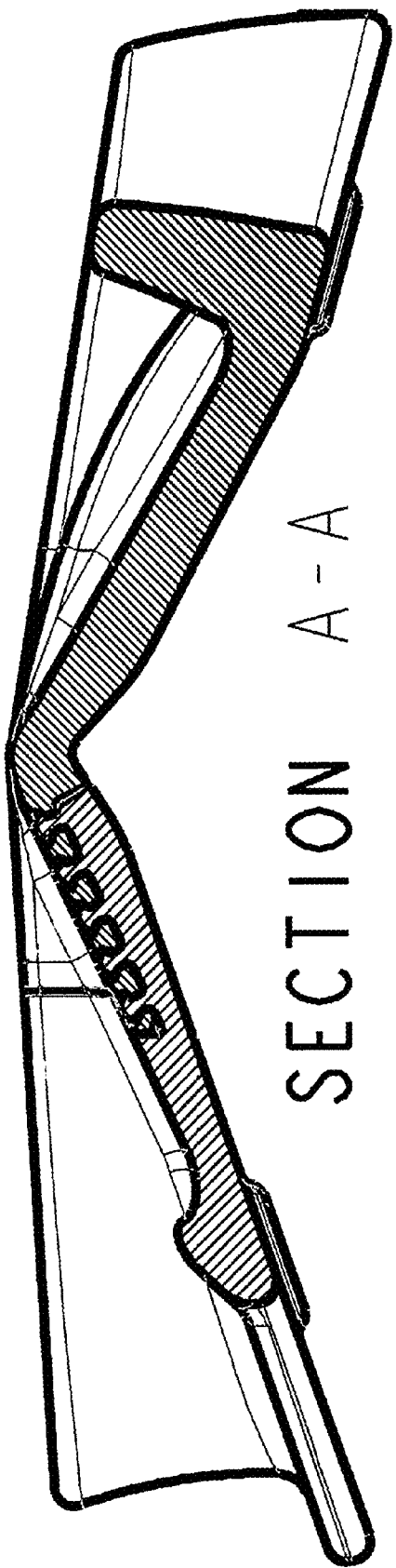
FIG. 7D shows enlarged schematic details of the incremental mechanism with taps and corresponding holes in just one of the members at sectional view along line A-A in FIG. 7C.
Figure 8A:
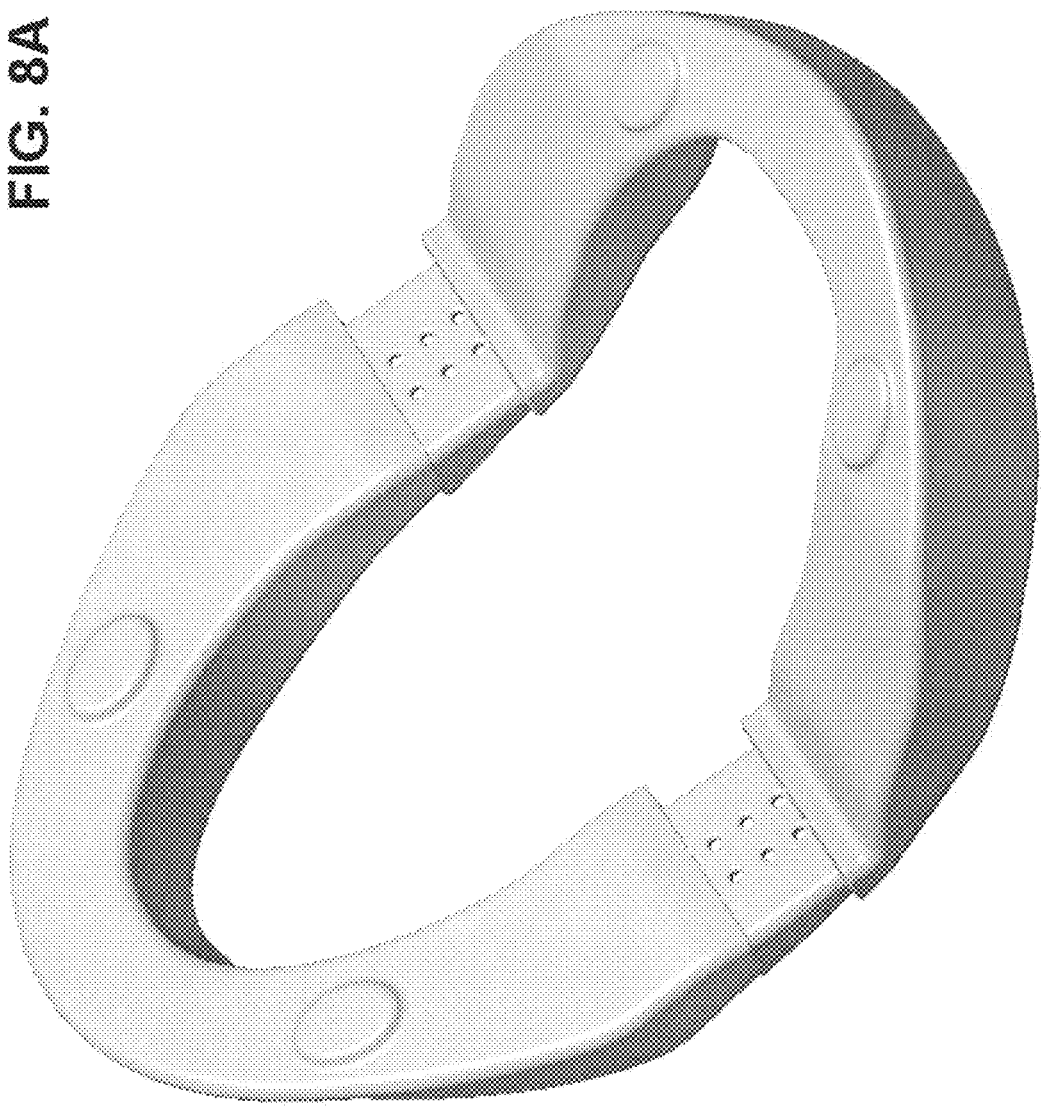
FIG. 8A shows the single member adjustable incremental version of the adjustable mandibular advancement device top view in an oblique perspective in its maximal elongated position.
Figure 9A:
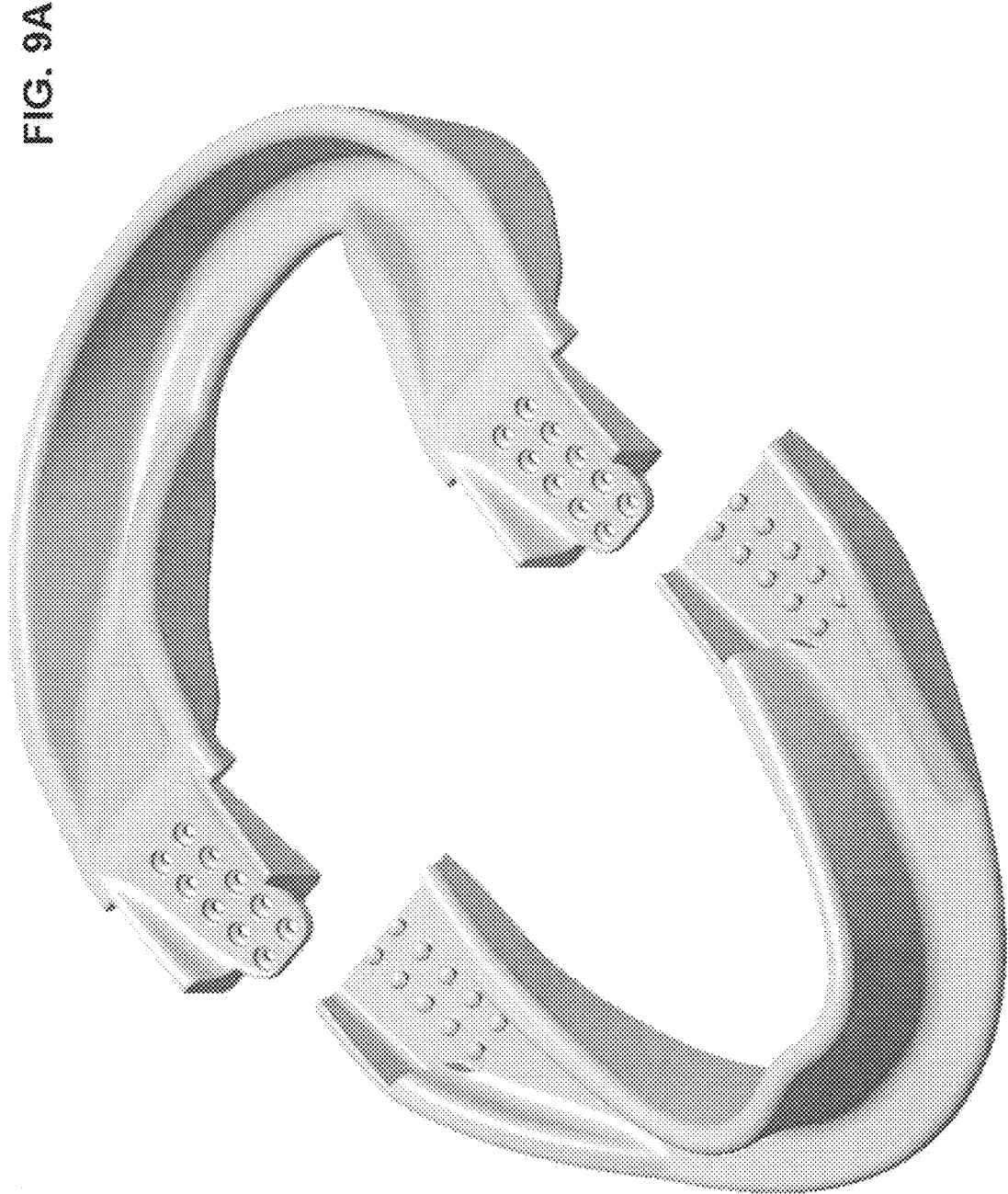
FIG. 9A shows the single member adjustable incremental version of the adjustable mandibular advancement device bottom view in an oblique perspective with detached members.
Figure 9B:
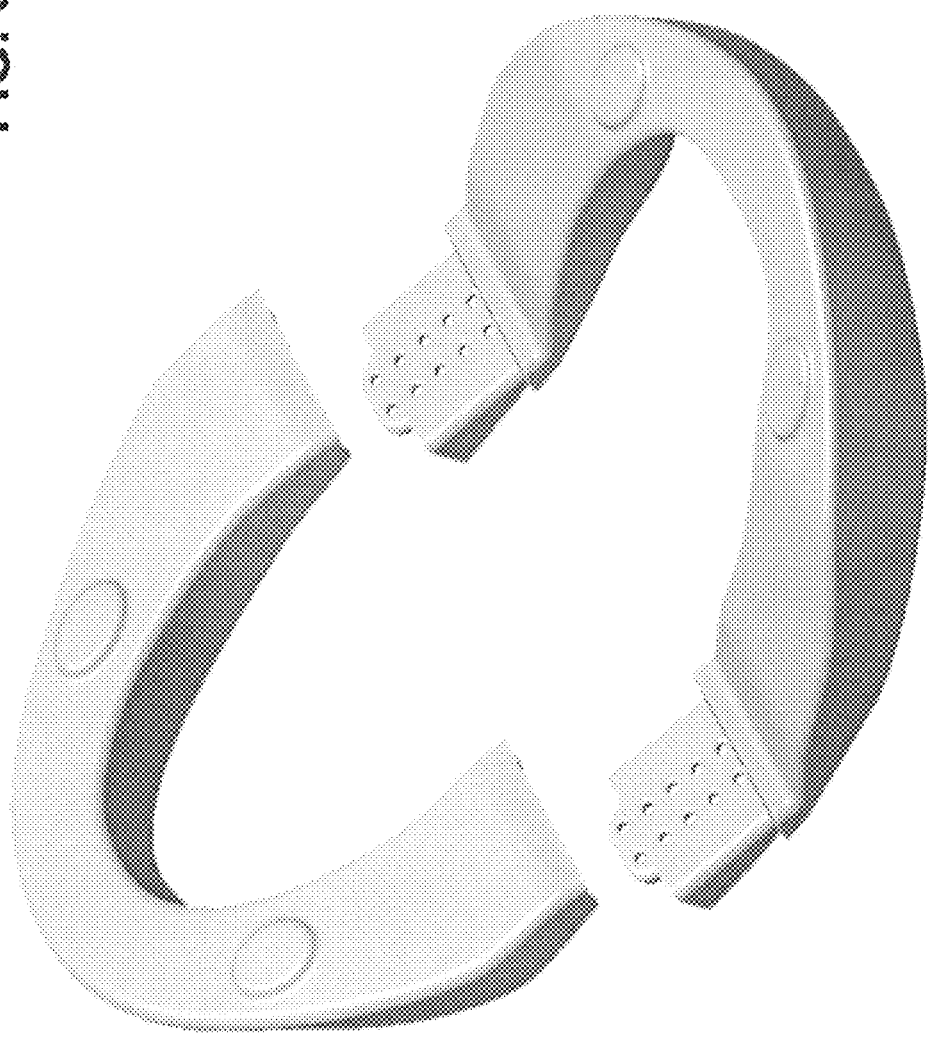
FIG. 9B shows the single member adjustable incremental version of the adjustable mandibular advancement device top view in an oblique perspective with detached members.
Figure 9C:
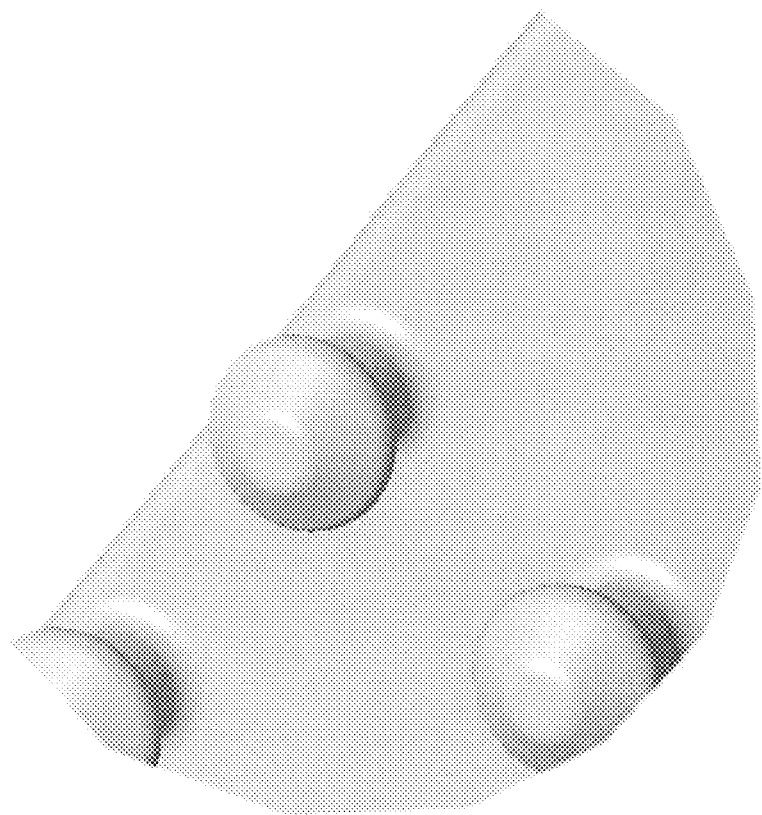
FIG. 9C shows in detail the knob part of the incremental mechanism of FIG. 9A.
Figure 9D:
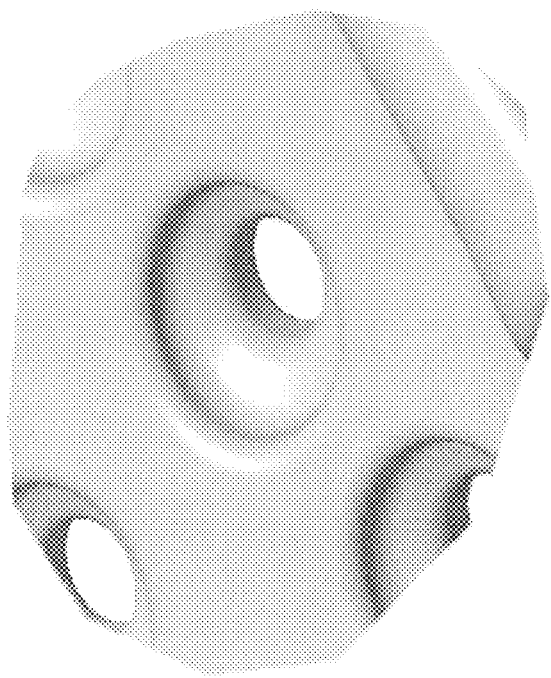
FIG. 9D shows in detail the hole part of the incremental mechanism of FIG. 9A.
Figure 10:
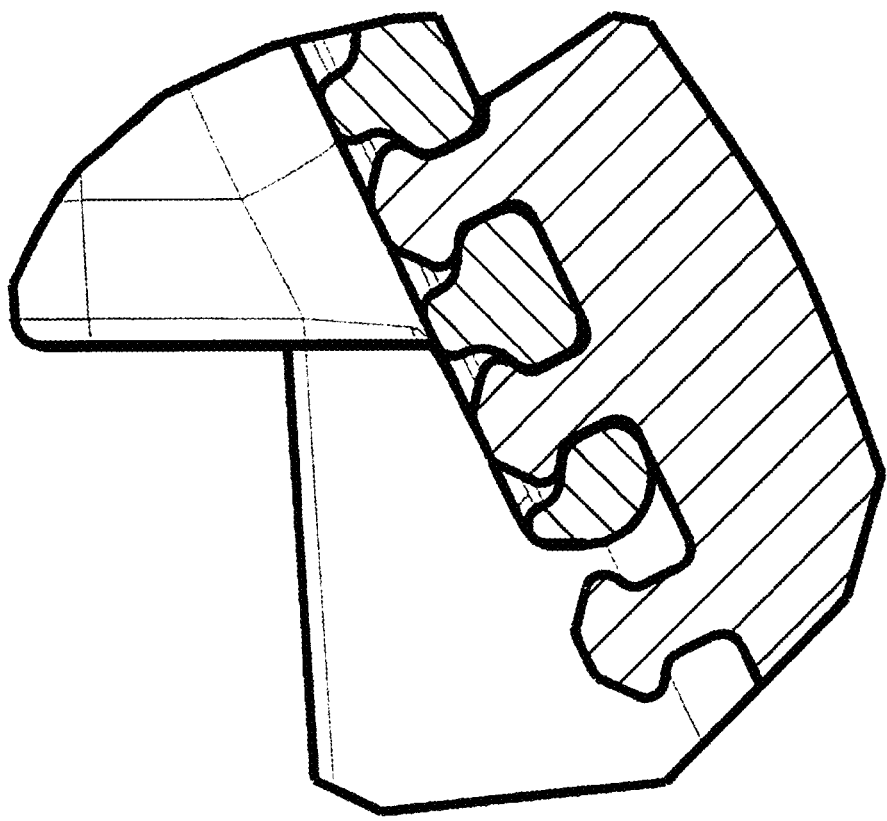
FIG. 10 shows an enlarged portion of FIG. SE illustrating the griping mechanism in its maximum enlarged stage.
Figure 12A:
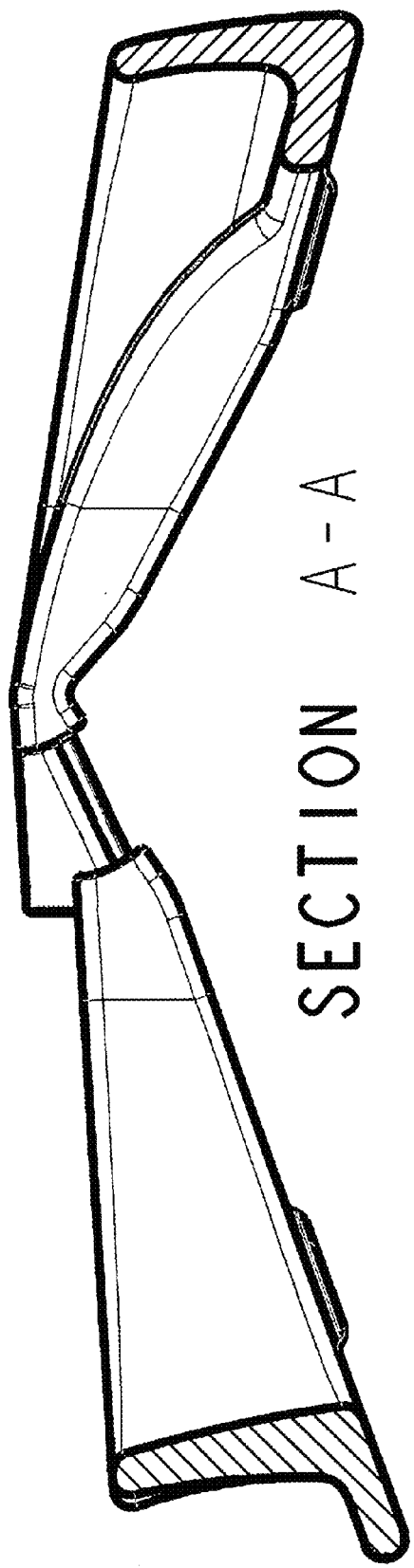
FIG. 12A shows a sectional view along line A-A in FIG. 11C at its maximum elongation at the midline of the device.
Figure 12B:
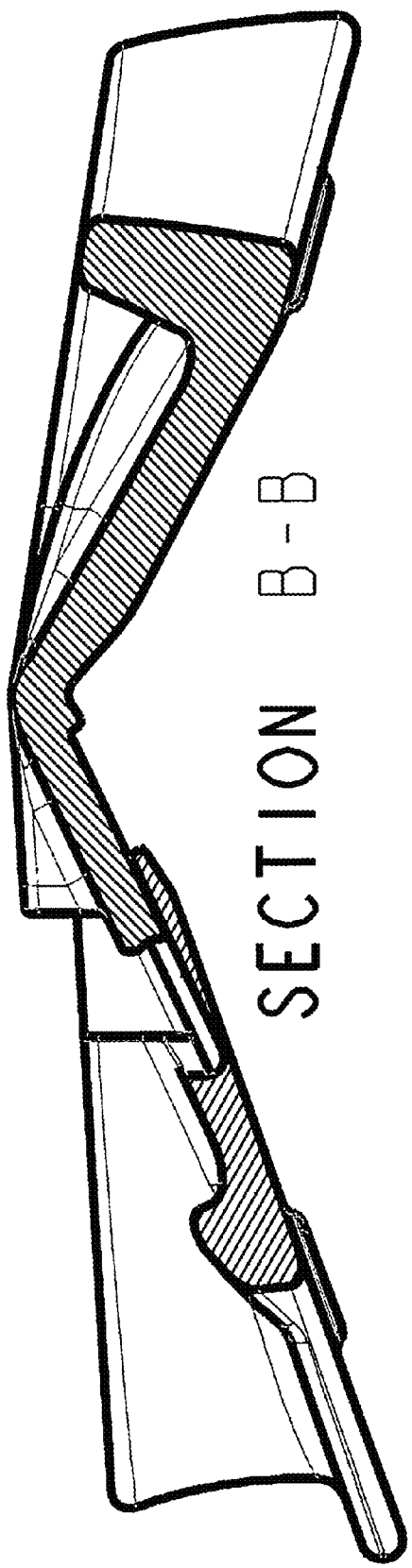
FIG. 12B shows a sectional view along line B-B in FIG. 11C at its maximum elongation at the junction of the device members.
Figure 12C:
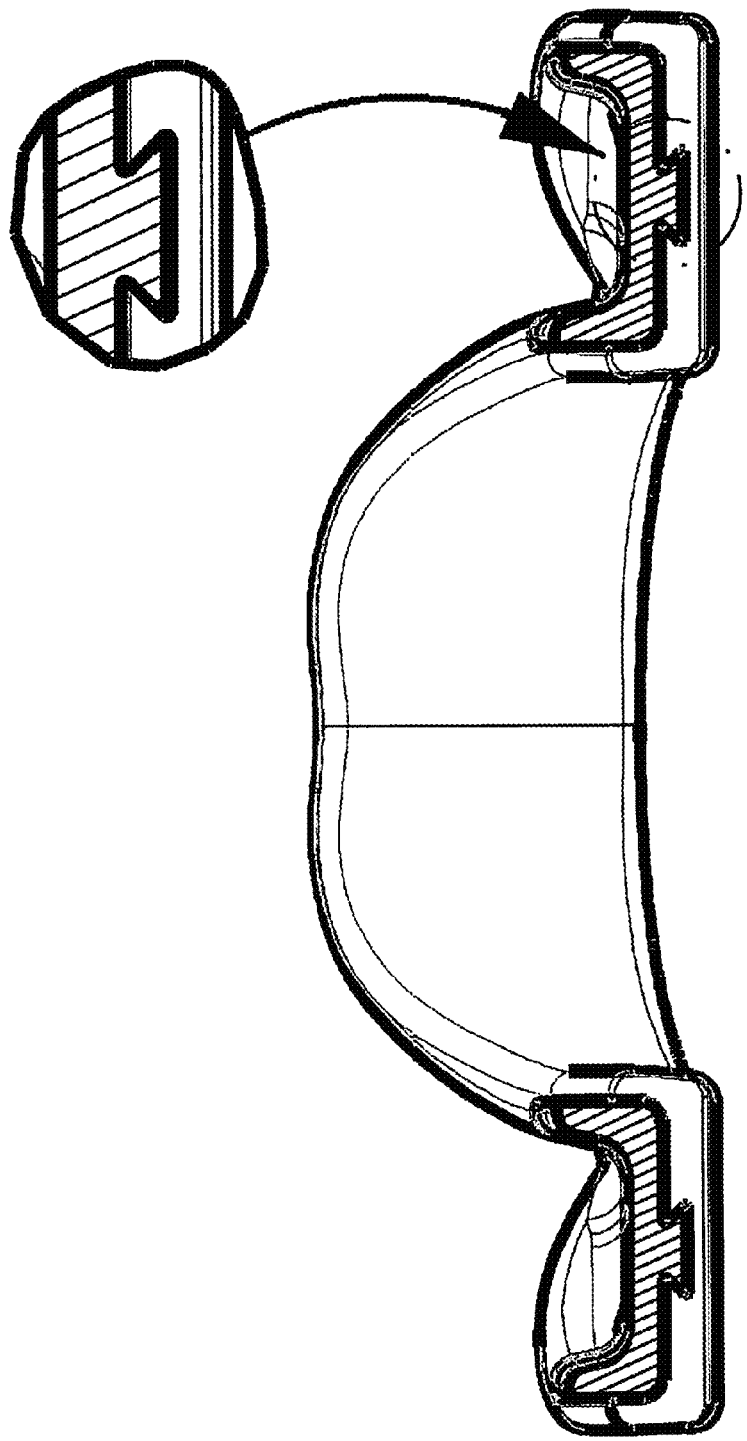
FIG. 12C shows the sectional view along line C-C in FIG. 1 IC in which the engaging mechanism can be seen, further in detailed insert.
Figure 13A:
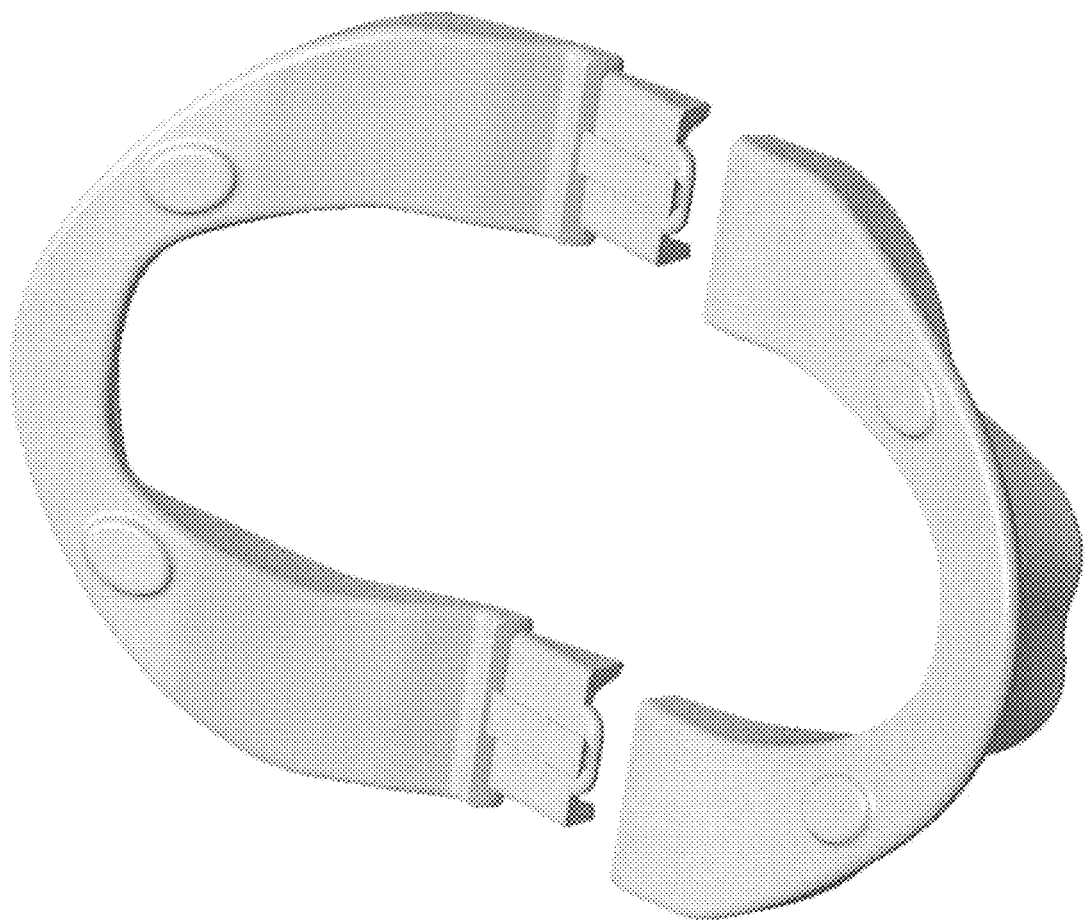
FIG. 13A shows the successive version of the mandibular advancement device in which a sliding system is indicated and where the sliding system here is in the form of a "dovetail guide structure" and is seen from an oblique perspective from the top in its detached situation.
Figure 13B:
FIG. 13B shows the successive version of the mandibular advancement device in which a sliding system is indicated and where the sliding system here is in the form of a "dovetail guide structure" and is seen from an oblique perspective from the top in its detached situation.
Figure 13C:
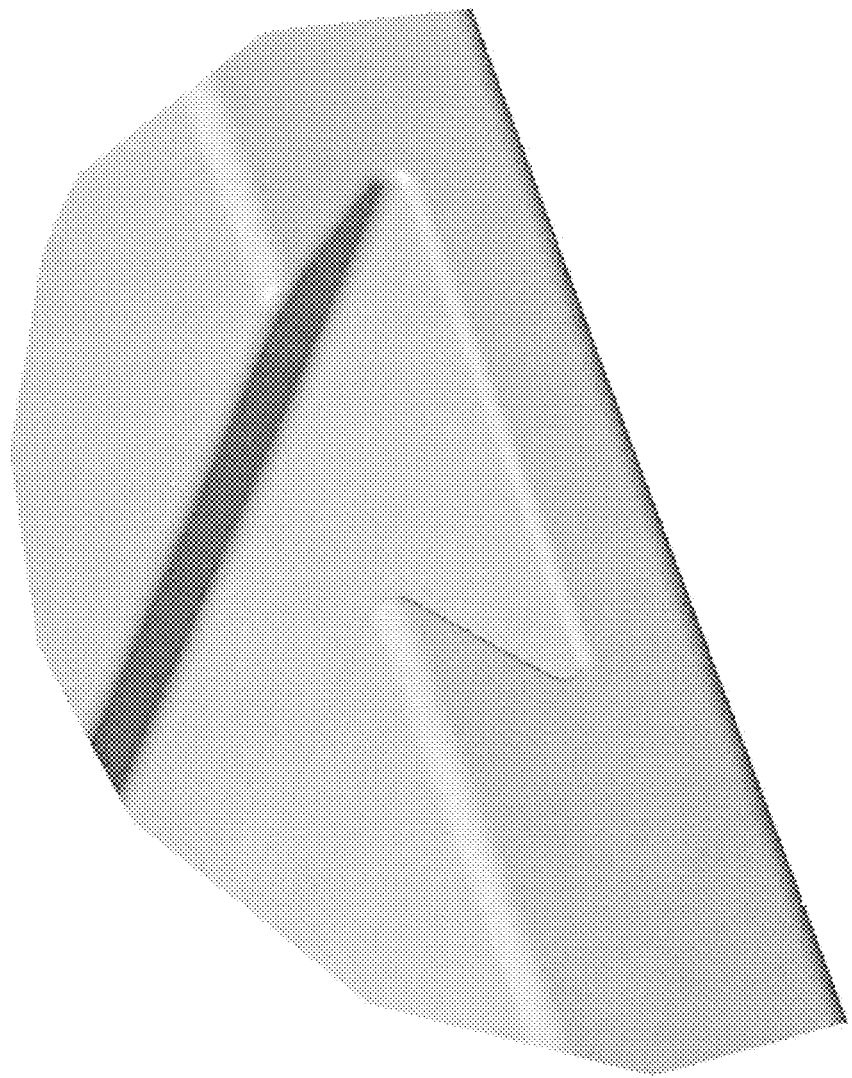
FIG. 13C shows a detailed enlargement of the negative structure of the successive adjustable sliding mechanism depicted as a "dovetail guide"
Figure 13D:
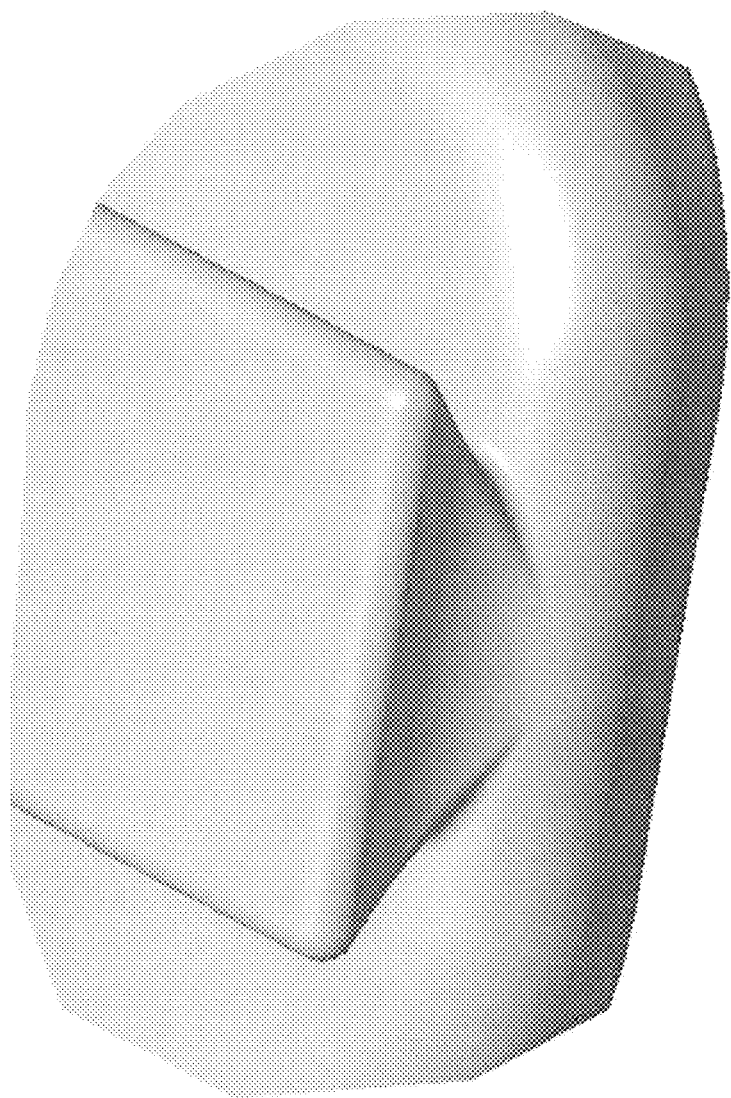
FIG. 13D shows a detailed enlargement of the positive structure of the successive adjustable sliding mechanism depicted as a positive structure.
Figure 14C:
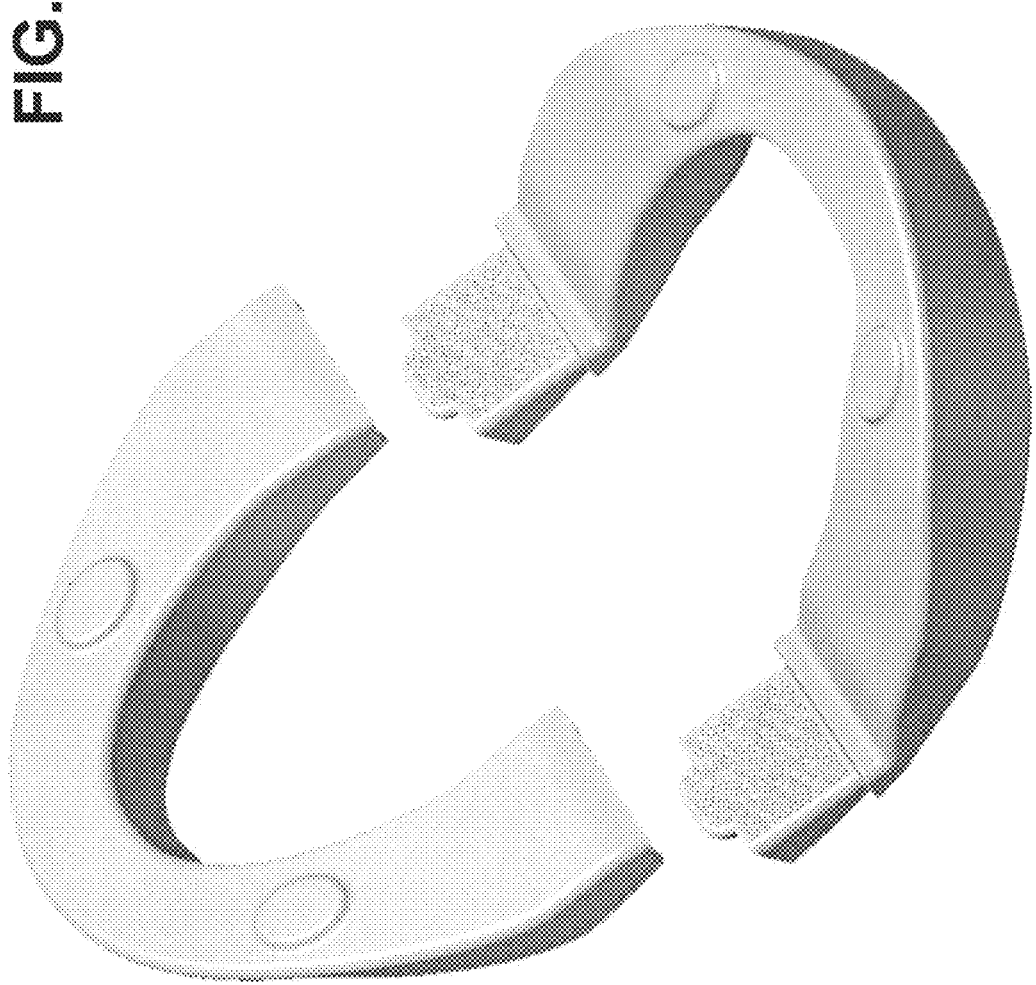
FIG. 14C shows the successive version of the adjustable mandibular advancement device top view in a oblique perspective in its detached position with visible platforms for the engagement of one part of the hook and loop system or a glue.
Figure 14D:
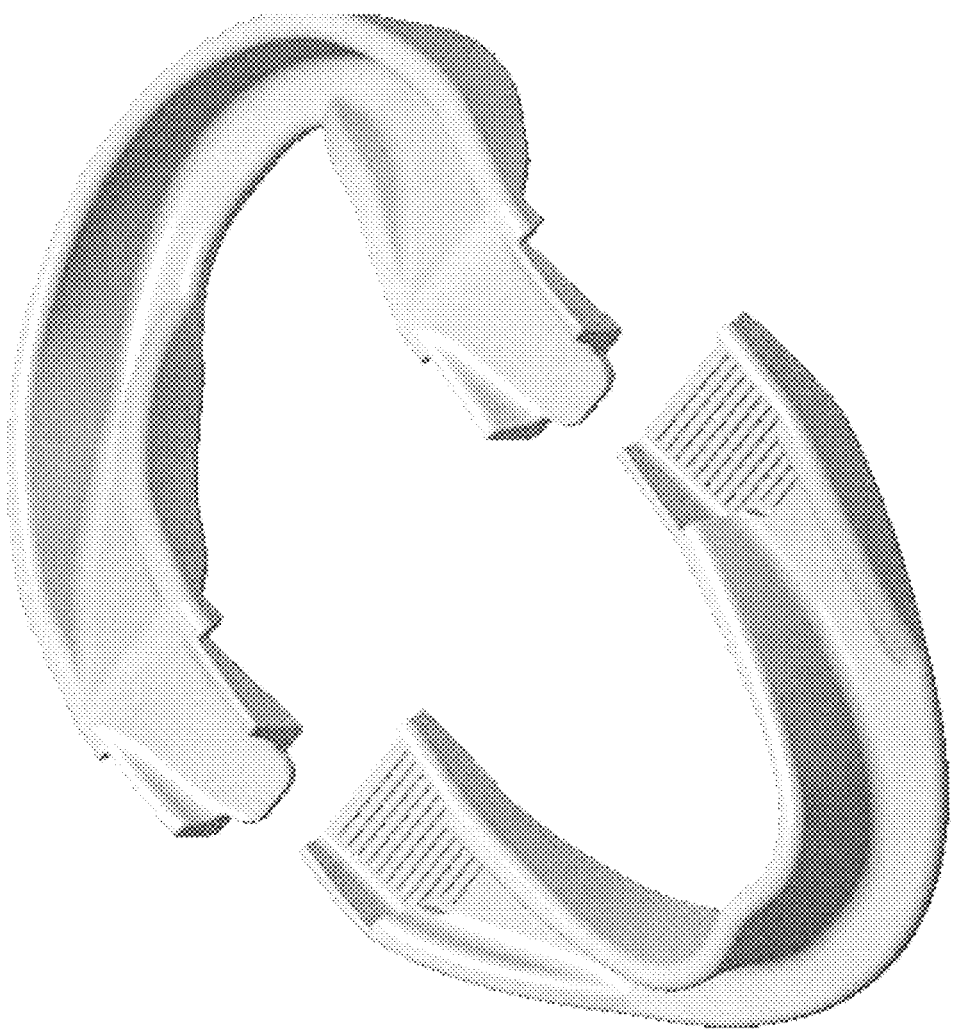
FIG. 14D shows the successive version of the adjustable mandibular advancement device bottom view in a oblique perspective in its detached position with visible platforms for the engagement of one part of the hoop and loop system or a glue.
Figure 14E:
FIG. 14E shows enlarged detail of one part of the connecting platforms on either upper mandibular or lower mandibular to engage with its corresponding counterpart by hook and loop system or a glue.
Figure 14F:
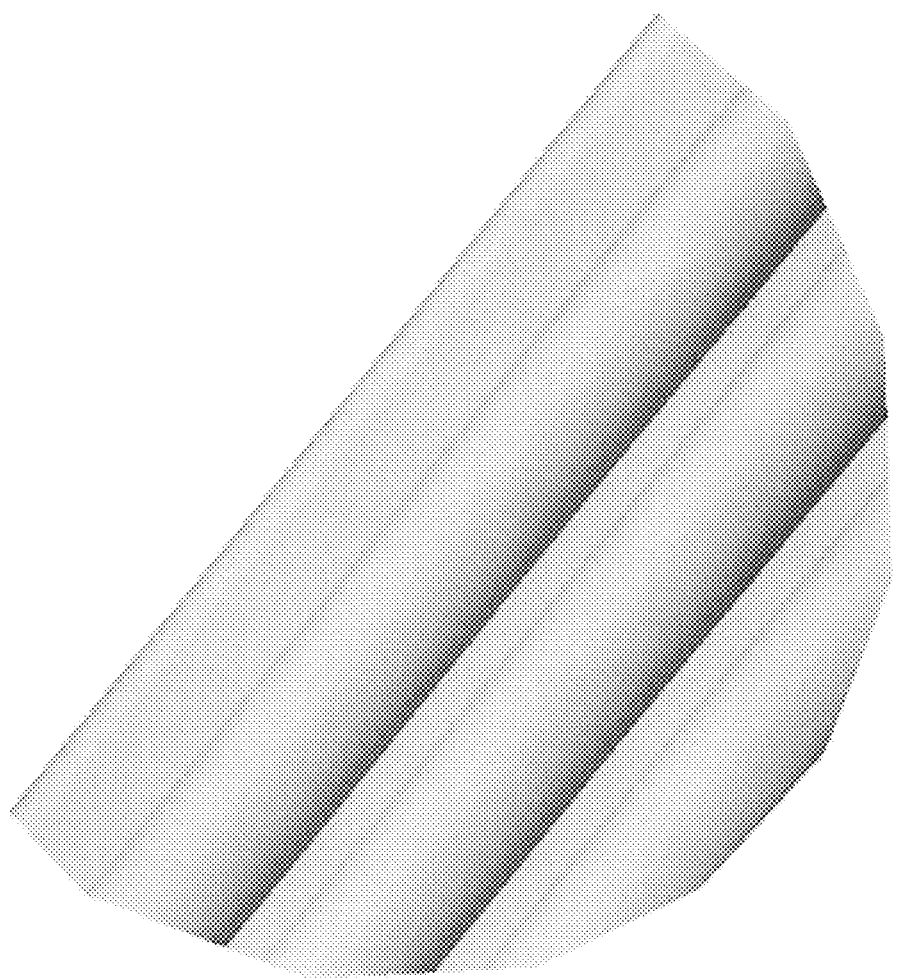
FIG. 14F shows enlarged illustration of the other part of the connecting platforms on either upper mandibular or lower mandibular to engage with its corresponding counterpart by hook and loop system or a glue.

FIGS. 1A-16 illustrate an anti-snoring and obstructive sleep apnea preventing device 10 for a human. The human has an upper jaw and a lower jaw. The upper jaw supports a maxillary dentition. The lower jaw supports a mandibulary dentition. The human has a nasopharynx, a oropharynx and a hypopharynx defining an airway passage.

In FIGS. 1A-6H, the device 10 comprises an upper maxillary member 20 defining a first general U-shape 22 extending between a first end 24 and a second end 26 adapted to engage the maxillary dentition of the human. A lower mandibulary member 40 defines a second general U-shape 42 extending between a first end 44 and a second end 46 adapted to engage the mandibulary dentition of the human.

A first maxillary incremental platform 30 extends from the first end 24 of the first general U-shape 22. A second maxillary incremental platform 32 extends from the second end 26 of the first general U-shape 22. A first mandibulary incremental platform 50 extends from the first end 44 of the second general U-shape 42. A second mandibulary incremental platform 52 extends from the second end 46 of the second generally U-shape 42.

A first plurality of incremental mechanisms 34 are coupled to the first maxillary incremental platform 30. A second plurality of incremental mechanisms 36 are coupled to the second maxillary incremental platform 32. A third plurality of incremental mechanisms 54 are coupled to the first mandibulary incremental platform 50. A fourth plurality of incremental mechanisms 56 are coupled to the second mandibulary incremental platform 52.

A first hinge mechanism 60 includes a first hinge 62 between a first hinge incremental platform 64 and a second hinge incremental platform 66. A second hinge mechanism 70 includes a second hinge 72 between a third hinge incremental platform 74 and a fourth hinge incremental platform 76.

A fifth plurality of incremental mechanisms 80 are coupled to the first hinge incremental platform 64. A sixth plurality of incremental mechanisms 82 are coupled to the second hinge incremental platform 66. A seventh plurality of incremental mechanisms 84 are coupled to the third hinge incremental platform 74. An eighth plurality of incremental mechanisms 86 are coupled to the fourth hinge incremental platform 76.

The first plurality of incremental mechanisms 34 engage with the fifth plurality of incremental mechanisms 80 for defining a first multiple stepwise snap on and snap off couple 90 of the first end 24 of the upper maxillary member 20 with the first hinge mechanism 60. The second plurality of incremental mechanisms 36 engage with the sixth plurality of incremental mechanisms 82 for defining a second multiple stepwise snap on and snap off couple 92 of the second end 26 of the upper maxillary member 20 with the second hinge mechanism 70. The third plurality of incremental mechanisms 54 engages with the seventh plurality of incremental mechanisms 84 for defining a third multiple stepwise snap on and snap off couple 94 of the first end 44 of the lower mandibulary member 40 with the first hinge mechanism 60. The fourth plurality of incremental mechanisms 56 engages with the eighth plurality of incremental mechanisms 86 for defining a fourth multiple stepwise snap on and snap off couple 96 of the second end 26 of the lower mandibulary member 40 with the second hinge mechanism 70.

The first hinge 62 pivots the first end 24 of the upper maxillary member 20 with the first end 44 of the lower mandibulary member 40. The second hinge 72 pivots the second end 26 of the upper maxillary member 20 with the second end 46 of the lower mandibulary member 40. The first hinge 62 and the second hinge 72 allow movement of the lower jaw relative to the upper jaw.

The first multiple stepwise snap on and snap off couple 90, the second multiple stepwise snap on and snap off couple 92, the third multiple stepwise snap on and snap off couple 94 and the fourth multiple stepwise snap on and snap off couple 96 define a griping mechanism 100 with an incremental adjustment 102 for positioning the upper maxillary member 20 relative to the lower mandibulary member 40 between a neutral position 104 and a maximum position 106 and retaining a forward position of the lower jaw relative to the upper jaw for keeping the airway passage in the nasopharynx, the oropharynx and the hypopharynx substantially free of occlusions.

The neutral position 104 defines a first general ellipse 110 with the upper maxillary member 20 and the lower mandibulary member 40. The maximum position 106 defines a second general ellipse 112 with the upper maxillary member 20 and the lower mandibulary member 40. The second general ellipse 112 has a greater area than the first general ellipse 110 for retaining a forward position of the lower jaw relative to the upper jaw for keeping the airway passage in the nasopharynx, the oropharynx and the hypopharynx substantially free of occlusions.

The first plurality of incremental mechanisms 34 may include a first plurality of knobs 120. The second plurality of incremental mechanisms 36 may include a second plurality of knobs 122. The third plurality of incremental mechanisms 54 may include a third plurality of knobs 124. The fourth plurality of incremental mechanisms 56 may include a fourth plurality of knobs 126. The fifth plurality of incremental mechanisms 80 may include a first plurality of holes 130. The sixth plurality of incremental mechanisms 82 may include a second plurality of holes 132. The seventh plurality of incremental mechanisms 84 may include a third plurality of holes 134. The eighth plurality of incremental mechanisms 86 may include a fourth plurality of holes 136.

The device 10 may further include a primary exterior maxillary wall 150 extending from the first maxillary incremental platform 30. A primary interior maxillary wall 152 extends from the first maxillary incremental platform 30. A secondary exterior maxillary wall 154 extends from the second maxillary incremental platform 32. A secondary interior maxillary wall 156 extends from the second maxillary incremental platform 32.

A primary exterior mandibulary wall 160 extends from the first mandibulary incremental platform 50. A primary interior mandibulary wall 162 extends from the first mandibulary incremental platform 50. A secondary exterior mandibulary wall 164 extends from the second mandibulary incremental platform 52. A secondary interior mandibulary wall 166 extends from the second mandibulary incremental platform 52.

A primary exterior hinge wall 170 extends from the first hinge incremental platform 64. A primary interior hinge wall 172 extends from the first hinge incremental platform 64. A secondary exterior hinge wall 174 extends from the second hinge incremental platform 66. A secondary interior hinge wall 176 extends from the second hinge incremental platform 66. A primary exterior hinge wall 180 extends from the third hinge incremental platform 74. A primary interior hinge wall 182 extends from the third hinge incremental platform 74. A secondary exterior hinge wall 184 extends from the fourth hinge incremental platform 76. A secondary interior hinge wall 186 extends from the fourth hinge incremental platform 76.

The primary exterior maxillary wall 150 abuts the primary exterior hinge wall 170 of the first hinge 62, the primary interior maxillary wall 152 abuts the primary interior hinge wall 172 of the first hinge 62, the primary exterior mandibulary wall 160 abuts the secondary exterior hinge wall 174 of the first hinge 62 and the primary interior mandibulary wall 162 abuts the secondary interior hinge wall 176 of the first hinge 62 for defining a second griping mechanism 190 and third griping mechanism 192 respectively.

The secondary exterior maxillary wall 154 abuts the primary exterior hinge wall 180 of the second hinge 72, the secondary interior maxillary wall 156 abuts the primary interior hinge wall 182 of the second hinge 72, the secondary exterior mandibulary wall 164 abuts the secondary exterior hinge wall 184 of the second hinge 72 and the secondary interior mandibulary wall 166 abuts the secondary interior hinge wall 186 of the second hinge 72 for defining a fourth griping mechanism 194 and a fifth griping mechanism 196 respectively.

An anterior wall 200 may be coupled to the upper maxillary member 20 for contacting the upper jaw. A posterior wall 202 may further be coupled to the lower mandibulary member 40 for contacting the lower jaw.

FIGS. 7A-10 illustrate an alternative embodiment of the device 10 comprises an upper maxillary member 20 defining a first general U-shape 22 extending between a first end 24 and a second end 26 adapted to engage the maxillary dentition of the human. A lower mandibulary member 40 defines a second general U-shape 42 extending between a first end 44 and a second end 46 adapted to engage the mandibulary dentition of the human.

A first maxillary incremental platform 30 extends from the first end 24 of the first general U-shape 22. A second maxillary incremental platform 32 extends from the second end 26 of the first general U-shape 22. A first mandibulary incremental platform 50 extends from the first end 44 of the second general U-shape 42. A second mandibulary incremental platform 52 extends from the second end 46 of the second generally U-shape 42.

A first plurality of incremental mechanisms 34 are coupled to the first maxillary incremental platform 30. A second plurality of incremental mechanisms 36 are coupled to the second maxillary incremental platform 32. A third plurality of incremental mechanisms 54 are coupled to the first mandibulary incremental platform 50. A fourth plurality of incremental mechanisms 56 are coupled to the second mandibulary incremental platform 52.

The first plurality of incremental mechanisms 34 engage with the third plurality of incremental mechanisms 54 for defining a primary multiple stepwise snap on and snap off couple 220 of the first end 24 of the upper maxillary member 20 with the first end 44 of the lower mandibulary member 40. The second plurality of incremental mechanisms 36 engage with the fourth plurality of incremental mechanisms 56 for defining a secondary multiple stepwise snap on and snap off couple 222 of the second end 26 of the upper maxillary member 20 with the second end 46 of the lower mandibulary member 40.

A first hinge 224 is positioned adjacent to the primary multiple stepwise snap on and snap off couple 220 for pivoting the first end 24 of the upper maxillary member 20 with the first end 44 of the lower mandibulary member 40. A second hinge 226 is positioned adjacent to the secondary multiple stepwise snap on and snap off couple 222 for pivoting the second end 26 of the upper maxillary member 20 with the second end 46 of the lower mandibulary member 40.

The first hinge 224 and the second hinge 226 allow movement of the lower jaw relative to the upper jaw. The primary multiple stepwise snap on and snap off couple 220 and the secondary multiple stepwise snap on and snap off couple 222 define a griping mechanism 100 with an incremental adjustment 102 for positioning the upper maxillary member 20 relative to the lower mandibulary member 40 between a neutral position 104 and a maximum position 106 and retaining a forward position of the lower jaw relative to the upper jaw for keeping the airway passage in the nasopharynx, the oropharynx and the hypopharynx substantially free of occlusions.

The neutral position 104 defines a first general ellipse 110 with the upper maxillary member 20 and the lower mandibulary member 40. The maximum position 106 defines a second general ellipse 112 with the upper maxillary member 20 and the lower mandibulary member 40. The second general ellipse 112 has a greater area than the first general ellipse 110 for retaining a forward position of the lower jaw relative to the upper jaw for keeping the airway passage in the nasopharynx, the oropharynx and the hypopharynx substantially free of occlusions.

The first plurality of incremental mechanisms 34 may include a first plurality of holes 130. The second plurality of incremental mechanisms 36 may include a second plurality of holes 132. The third plurality of incremental mechanisms 54 may include a first plurality of knobs 120. The fourth plurality of incremental mechanisms 56 may include a second plurality of knobs 122.

A primary exterior maxillary wall 150 extends from the first maxillary incremental platform 30. A primary interior maxillary wall 152 extends from the first maxillary incremental platform 30. A secondary exterior maxillary wall 154 extends from the second maxillary incremental platform 32. A secondary interior maxillary wall 156 extends from the second maxillary incremental platform 32. A primary exterior mandibulary wall 160 extends from the first mandibulary incremental platform 50. A primary interior mandibulary wall 162 extends from the first mandibulary incremental platform 50. A secondary exterior mandibulary wall 164 extends from the second mandibulary incremental platform 52. A secondary interior mandibulary wall 166 extends from the second mandibulary incremental platform 52.

The primary exterior maxillary wall 150 abuts the primary exterior mandibulary wall 160 and the primary interior maxillary wall 152 abuts the primary interior mandibulary wall 162 for defining a second griping mechanism 190. The secondary exterior maxillary wall 154 abuts the secondary exterior mandibulary wall 164 and the secondary interior maxillary wall 156 abuts the secondary interior mandibulary wall 166 for defining a third griping mechanism 192.

An anterior wall 200 may be coupled to the upper maxillary member 20 for contacting the upper jaw. A posterior wall 202 may be coupled to the lower mandibulary member 40 for contacting the lower jaw.

FIGS. 11A-13D illustrate an alternative embodiment of the device 10 comprises an upper maxillary member 20 defining a first general U-shape 22 extending between a first end 24 and a second end 26 adapted to engage the maxillary dentition of the human. A lower mandibulary member 40 defines a second general U-shape 42 extending between a first end 44 and a second end 46 adapted to engage the mandibulary dentition of the human.

A first maxillary successive platform 240 extends from the first end 24 of the first general U-shape 22. A second maxillary successive platform 242 extends from the second end 26 of the first general U-shape 22. A first mandibulary successive platform 244 extends from the first end 44 of the second general U-shape 42. A second mandibulary successive platform 246 extends from the second end 46 of the second generally U-shape 42.

A first successive mechanism 250 is coupled to the first maxillary successive platform 240. A second successive mechanism 252 is coupled to the second maxillary successive platform 242. A third successive mechanism 254 is coupled to the first mandibulary successive platform 244. A fourth successive mechanism 256 is coupled to the second mandibulary successive platform 246.

The first successive mechanism 250 engages with the third successive mechanism 254 for defining a primary successive couple 260 of the first end 24 of the upper maxillary member 20 with the first end 44 of the lower mandibulary member 40. The second successive mechanism 252 engages with the fourth successive mechanism 256 for defining a secondary successive couple 262 of the second end 26 of the upper maxillary member 20 with the second end 46 of the lower mandibulary member 40.

A first hinge 62 is positioned adjacent to the primary successive couple 260 for pivoting the first end 24 of the upper maxillary member 20 with the first end 44 of the lower mandibulary member 40. A second hinge 72 is positioned adjacent to the secondary successive couple 262 for pivoting the second end 26 of the upper maxillary member 20 with the second end 46 of the lower mandibulary member 40.

The first hinge 62 and the second hinge 72 allow movement of the lower jaw relative to the upper jaw. The primary successive couple 260 and the secondary successive couple 262 define a successive adjustment 264 for positioning the upper maxillary member 20 relative to the lower mandibulary member 40 between a neutral position 104 and a maximum position 106 and retaining a forward position of the lower jaw relative to the upper jaw for keeping the airway passage in the nasopharynx, the oropharynx and the hypopharynx substantially free of occlusions.

The neutral position 104 defines a first general ellipse 110 with the upper maxillary member 20 and the lower mandibulary member 40. The maximum position 106 defines a second general ellipse 112 with the upper maxillary member 20 and the lower mandibulary member 40. The second general ellipse 112 has a greater area than the first general ellipse 110 for retaining a forward position of the lower jaw relative to the upper jaw for keeping the airway passage in the nasopharynx, the oropharynx and the hypopharynx substantially free of occlusions.

The first successive mechanism 250 may include a first male dovetail 270. The second successive mechanism 252 may include a second male dovetail 272. The third successive mechanism 254 may include a first female dovetail 274. The fourth successive mechanism 256 may include a second female dovetail 276.

FIGS. 14A-14F illustrate an alternative embodiment of the device 10 wherein the first successive mechanism 250 includes a first plurality of hooks 280. The second successive mechanism 252 includes a second plurality of hooks 282. The third successive mechanism 254 includes a first plurality of loops 284. The fourth successive mechanism 256 includes a second plurality of loops 286. Alternatively, the first successive mechanism 250 includes a first glue 290. The second successive mechanism 252 includes a second glue 292. The third successive mechanism 254 includes a third glue 294. The fourth successive mechanism 256 includes a fourth glue 296.

A primary exterior maxillary wall 150 extends from the first maxillary successive platform 30. A primary interior maxillary wall 152 extends from the first maxillary successive platform 30. A secondary exterior maxillary wall 154 extends from the second maxillary successive platform 32. A secondary interior maxillary wall 156 extends from the second maxillary successive platform 32. A primary exterior mandibulary wall 160 extends from the first mandibulary successive platform 50. A primary interior mandibulary wall 162 extends from the first mandibulary successive platform 50. A secondary exterior mandibulary wall 164 extends from the second mandibulary successive platform 52. A secondary interior mandibulary wall 166 extends from the second mandibulary successive platform 52.

The primary exterior maxillary wall 150 abuts the primary exterior mandibulary wall 160 and the primary interior maxillary wall 152 abuts the primary interior mandibulary wall 162 for defining a second griping mechanism 190. The secondary exterior maxillary wall 154 abuts the secondary exterior mandibulary wall 164 and the secondary interior maxillary wall 156 abuts the secondary interior mandibulary wall 166 for defining a third griping mechanism 192.

An anterior wall 200 may be coupled to the upper maxillary member 20 for contacting the upper jaw. A posterior wall 202 may be coupled to the lower mandibulary member 40 for contacting the lower jaw As shown in FIGS. 1A-16 illustrate the adjustable anti-snore device 10 according to the invention comprises an upper member 20 adapted to engage the maxillary dentition of a human and a lower member 40 adapted to engage the mandibulary dentition of the human. The upper 20 and lower members 40 being resiliently or mechanically hinged together, wherein the resiliency of the hinges are adapted to allow the physiological movement of the lower jaw in the sagital plane while retaining a forward position of the lower jaw relative to the upper jaw and thereby keeping the airway passage in the nasopharynx, the oropharynx and the hypopharynx substantially free of occlusion, while at the same time embody the adjustability in one or two form, i.e. incremental and/or successive.

The device 10 according to the invention combines three essential functions: the forward positioning of the lower jaw relative to the upper jaw, the hinging, and the adjustability of the sagital relation between the two members. As will be explained below, the forward positioning of the lower jaw is essential to prevent occlusion of the airway passage in the pharyngeal space during sleep. The resilient or mechanically hinging makes it possible and realistic to maintain the forward positioning of the lower jaw even during movements in the sagital plane which unavoidably occur during sleep. And the adjustability makes it useful for even the smallest and the largest person wearing the device. This essential combination of features which ensures constant non-constricted airflow and unrestricted movement in the sagital plane and thereby ensures a constant efficient function without risk of the device falling out of the mouth of the user and without any substantial discomfort together with the adjustability which even allows some horizontal movements, distinguishes the device according to the invention from all of the abovementioned prior art devices.

The device according to the invention may be made of any material, such as metal, alloy, wood, plastics, etc. provided that the device made feels soft and comfortable in the mouth without any constriction or damaging of the tissue, such as gums, tongue, teeth, but at the same time is sufficiently capable of retaining its shape and of exerting a sufficient resiliency towards the muscular tension and forces acted upon the jaws so that it will maintain the lower jaw in the anterior position while allowing normal movements during sleep. The material used for the device according to the invention should not contain any allergens or other kind of toxic ingredients.

The device according to the invention is preferably made of a resilient non-toxic plastics material, such as a polyvinyl resin, including a vinyl acetate-ethylene copolymer such as poly (ethyl vinyl acetate), or a polyolefin such as polyethylene or polypropylene.

It is particularly preferred that the resilient non-toxic plastics material is a thermoplastic material, such as a cellulose derivative, a vinyl polymer, a polystyrene, a polyamide, an acrylic resin, etc., which can be shaped to adapt to an individual dentition by moderate heating, such as heating to a temperature above normal human body temperature, that is, a temperature of at least 40° C. and at the most 80° C., e.g. about 70° C. The material presently most preferred by the inventor is ethylene vinyl acetate copolymer.

The device according to the present invention may be manufactured by plastics molding, such as cold molding, compression molding, injection molding, etc. The manufacturing method presently most preferred by the inventor is injection molding.

The upper 20 and lower members 40 are preferably integrated with each other through resilient hinges 62, 72 made of the same material as the upper 20 and lower members 40. However, the hinges 62, 72 may be reinforced and their resiliency enhanced by insertion, such as cast in, etc., into the hinges 62, 72 of a resilient member, such as a resilient plastics member, a metallic resilient member, such as a flat spring, a laminated spring etc. etc., or simply by a mechanical connection.

The adjustability according to this invention, being embedded or glued, gilded or otherwise attached to the membering parts for the engagement of the dentition, in the upper maxillary member 20, the lower mandibulary member 40 or both members at the same time, being either incremental 102 or successive 264.

As it will be understood the adjustability may be embedded in the anterior parts of the upper 20 and/or lower members 40 of the device 10 thus keeping the resilient or mechanic hinge 62, 72 intact.

The adjustability of the protrusion of the mandible relative to the maxilla is made adjustable by the means of embedding a positive structure in either the forward moving part of the device and a negative structure in the stable part of the device or vice versa. The positive part may be constructed as a knob, rod, hook or alike, whereas the corresponding negative structures would be holes, cylinders and loops in this aspect. Other configurations may apply. Thus depending on the structure selected, knob, rod or hook etc. the adjustability will express itself as either incremental (stepwise) or successive (stepless).

When the successive 264 design is used, a special rod 300 can be supported for the consumer that allows fixation of the desired position of the forwarded device. The special rod 300 and alike may be made of a heat conducting metal 302 insulated with a non-heat conducting hand piece 304, so as not to damage the fingertips of the user when heating the rod 300 and penetrating the material of the invention at the desired position.

A particularly preferred way of shipping the device according to the invention to the end consumer is as a kit comprising the device 10 and a temperature indicator adapted to indicate a temperature change to an elevated temperature at which the material of the device 10 can be shaped. This makes it simple and safe for the end user to mold the device to conform to his or hers specific dentition simply by heating the relevant domain of the device in water at the temperature of which is kept in the correct temperature range for the material in question by using the indication of the temperature indicator.

It should be understood that the use of the anti-snore device according to the invention is not limited to prevention or reduction of snoring or OSAS but the device is applicable in any situation where it is desirable to secure free airway passage in human beings, such as during recovery from anesthesia, during unconsciousness, etc.

The unique combination of resilient/mechanic hinging, dentition engagement and adjustability discussed above can also, according to another aspect of the invention, be utilized in a device for relieving guided transpositions of the jaws.

In this latter aspect, the invention relates to an orthognatic function device comprising an upper member 20 adapted to engage with the maxillary dentition of a human and a lower member 40 adapted to engage with the mandibulary dentition of the human, the upper 20 and lower 40 members having bases which prevent direct contact between opposing teeth, thereby eliminating guided transposition of the jaw relation and the upper and lower members being resiliently hinged together in such a manner together with the adjustability that the lower jaw of the human is kept positioned in a normal position relative to the upper jaw, allowing vertical movement and, in the occluded intercuspidal position 310, allowing horizontal movement so that the temporo mandibular joint is kept substantially in its resting position, both when the lower jaw is at rest and when it is working.

It will be understood that also in this aspect, the resiliency of the hinging should be adapted to allow the physiological movement of the lower jaw in the sagital plane, and that the above comments concerning selection of suitable materials, manufacturing method, and adaptation to the individual dentition by shaping the material in a softened, e.g. heat-softened, condition apply also to this aspect of the invention.

Thus, the orthognatic aspect of the invention provides a completely new philosophy in relieving temporo mandibular joint disorders caused by irregular dentition: In contrast to known orthognatic devices, the orthognatic device according to the invention is hinged in such a way that no interference between the upper and lower members can occur, thereby alleviating symptoms caused by abnormal interference from irregular dentition. Furthermore, tensions caused by tooth grinding and clenching are alleviated. At the same time, this orthognatic device is much simpler to adapt to the individual needs of the person in question than conventional orthognatic devices, and it can even be used by the individual consumer without assistance by any professional.

The incremental 102 and successive 264 advancement anti-snoring device wherein the upper 20 and lower 40 members are resilient or mechanical hinged and the members are incrementally or successively adjustable to each other, whereby the hinging is adapted to allow physiological movements of the lower jaw in the sagital plane while retaining a forward position of the lower jaw relative to the upper jaw and thereby keeping the airway passage in the nasopharynx, the oropharynx and the hypopharynx substantially free of occlusion.

In shown in FIGS. 1A-10, the multiple stepwise incremental "snap-on-snap-of" structures 90, 92, 94, and 96 may be is made by male versus female parts of different forms such as round, square, hexagonal and so on, designed to engage with its corresponding opposite part of negative structural form. In addition, the multiple stepwise incremental positive snap-on structures may include a top carved (lobed) with variable numbers of segments. The multiple stepwise incremental negative snap-on structures are lobed with variable numbers of segments. The incremental 102 or successive 264 mechanism can be removed from the basic members of the device (upper maxillary, lower mandibulary and hinge), renewed, restored and reattached to the members again.

FIGS. 14A-14F illustrate the successive mechanism 264 made of interlocking structures like hooks and loops 280, 282, 284, 286, as in Velcro, where the mandibular part consists of hook and the opposing maxillary part consists of loops, or vice versa. The hooks and loops may include microscopic, mesoscopic or macroscopic in sizes. Preferably, the hooks and loops are made of another non-toxic material different from the material used for the main maxillary and mandibulary members to engage the dentition of the human. The successive mechanism 264 can be removed from the basic members of the device (upper maxillary, lower mandibulary and hinge), renewed, restored and reattached to the members again.

In another embodiment, the successive mechanism 264 may be constructed as a telescopic system, where one member is constructed as a cylinder and the other member is constructed as a rod or piston. Alternatively, the successive mechanism 264 may differ from the circular for, i.e. square, rectangle, dovetail 270, 272 etc., e.g. The cylinder and the piston rod are preferably made of another non-toxic material different from the material used for the main maxillary and mandibulary members to engage the dentition of the human. Alternatively, a glue 290 may be used to attach the device.

The device 10 is adapted to keep the lower jaw in the positions corresponding to the area between the intercuspidal position 312, the protruded contact position 314, and the maximum opening point 316 of the jaw. The device 10 is further adapted to keep the lower jaw substantially in the position corresponding to the anterior border of the physiological space of movement of the lower jaw as limited by the anatomical structures in the temporo mandibular joint. Preferably, the device 10 produces a forward displacement of the lower jaw in a range of 5 to 13 mm in the sagital plane and 6 to 35 mm in the vertical plane along the border of the IP-MOP curve.

The upper member 20 may have an anterior wall 200 adapted to be in contact with the facial surfaces of the incisors, canines and premolars of the upper jaw, and the lower member 40 may have a posterior wall 202 adapted to be in contact with the lingual surfaces of the incisors, canines and premolars of the lower jaw.

Preferably, the upper member 20 is substantially ellipsoid in shape in accordance with the normal dentition of a human, and the lower member 40 is substantially parabola in shape in accordance with the human dentition.

The device 10 may be constructed of a resilient non-toxic plastics material, such as polyvinyl resin, including a vinyl acetate-ethylene copolymer such ad poly (ethyl vinyl acetate) or a polyolefin such as polyethylene or polypropolene material. The non-toxic plastics material may include a thermoplastic material which can be shaped to adapt to an individual dentition by moderate heating. The temperature at which the material can be shaped is at least 40° C. and at the most 85° C., e.g. about 70° C.

Preferably, the upper 20 and lower 40 members are integrated with each other through resilient hinges made of the same material as the upper and lower members. The hinge 62 may be located in the most dorsal part of the device being embedded in or resilient due to the material itself. The most dorsal part of the hinge is convex at the most posterior part and concave at the most anterior part of the hinge when situated in the patients mouth.

The device 10 may incorporate a kit comprising the device 10 together with a temperature indicator adapted to indicate the temperature change to an elevated temperature at which the material of the device can be shaped individually. The kit may include a heatable metal rod 300 combined with an insulating hand piece 304 for the use of locking the sliding incremental process by means of penetration both members at the desired forward positioned maxillary member relative to the mandibulary member.

The invention claimed is:

1. An anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining an airway passage, the device comprising:

an upper maxillary member defining a first general U-shape extending between a first end and a second end adapted to engage the maxillary dentition of the human;

a lower mandibulary member defining a second general U-shape extending between a first end and a second end adapted to engage the mandibulary dentition of the human;

a first maxillary incremental platform extending from said first end of said first general U-shape;

a second maxillary incremental platform extending from said second end of said first general U-shape;

a first mandibulary incremental platform extending from said first end of said second general U-shape;

a second mandibulary incremental platform extending from said second end of said second generally U-shape;

a first plurality of incremental mechanisms coupled to said first maxillary incremental platform;

a second plurality of incremental mechanisms coupled to said second maxillary incremental platform;

a third plurality of incremental mechanisms coupled to said first mandibulary incremental platform;

a fourth plurality of incremental mechanisms coupled to said second mandibulary incremental platform;

a first hinge mechanism including a first hinge between a first hinge incremental platform and a second hinge incremental platform;

a second hinge mechanism including a second hinge between a third hinge incremental platform and a fourth hinge incremental platform;

a fifth plurality of incremental mechanisms coupled to said first hinge incremental platform;

a sixth plurality of incremental mechanisms coupled to said second hinge incremental platform;

a seventh plurality of incremental mechanisms coupled to said third hinge incremental platform;

an eighth plurality of incremental mechanisms coupled to said fourth hinge incremental platform;

said first plurality of incremental mechanisms engaging with said fifth plurality of incremental mechanisms for defining a first multiple stepwise snap on and snap off couple of said first end of said upper maxillary member with said first hinge mechanism;

said second plurality of incremental mechanisms engaging with said sixth plurality of incremental mechanisms for defining a second multiple stepwise snap on and snap off couple of said second end of said upper maxillary member with said second hinge mechanism;

said third plurality of incremental mechanisms engaging with said seventh plurality of incremental mechanisms for defining a third multiple stepwise snap on and snap off couple of said first end of said lower mandibulary member with said first hinge mechanism;

said fourth plurality of incremental mechanisms engaging with said eighth plurality of incremental mechanisms for defining a fourth multiple stepwise snap on and snap off couple of said second end of said lower mandibulary member with said second hinge mechanism;

said first hinge pivoting said first end of said upper maxillary member with said first end of said lower mandibulary member;

said second hinge pivoting said second end of said upper maxillary member with said second end of said lower mandibulary member;

said first hinge and said second hinge allowing movement of the lower jaw relative to the upper jaw; and said first multiple stepwise snap on and snap off couple, said second multiple stepwise snap on and snap off couple, said third multiple stepwise snap on and snap off couple and said fourth multiple stepwise snap on and snap off couple defining a griping mechanism with an incremental adjustment for positioning said upper maxillary member relative to said lower mandibulary member between a neutral position and a maximum position and retaining a forward position of the lower jaw relative to the upper jaw for keeping the airway passage in the nasopharynx, the oropharynx and the hypopharynx substantially free of occlusions.

2. An anti-snoring and obstructive sleep apnea preventing device as set forth in claim 1, wherein said neutral position defines a first general ellipse with said upper maxillary member and said lower mandibulary member;
said maximum position defines a second general ellipse with said upper maxillary member and said lower mandibulary member; and
said second general ellipse defining a greater area than said first general ellipse for retaining a forward position of the lower jaw relative to the upper jaw for keeping the airway passage in the nasopharynx, the oropharynx and the hypopharynx substantially free of occlusions.

3. An anti-snoring and obstructive sleep apnea preventing device as set forth in claim 1, wherein said first plurality of incremental mechanisms include a first plurality of knobs;
said second plurality of incremental mechanisms include a second plurality of knobs;
said third plurality of incremental mechanisms include a third plurality of knobs;
said fourth plurality of incremental mechanisms include a fourth plurality of knobs;
said fifth plurality of incremental mechanisms include a first plurality of holes;
said sixth plurality of incremental mechanisms include a second plurality of holes;
said seventh plurality of incremental mechanisms include a third plurality of holes; and
said eighth plurality of incremental mechanisms include a second plurality of holes.

4. An anti-snoring and obstructive sleep apnea preventing device as set forth in claim 1, further including a primary exterior maxillary wall extending from said first maxillary incremental platform;
a primary interior maxillary wall extending from said first maxillary incremental platform;
a secondary exterior maxillary wall extending from said second maxillary incremental platform;
a secondary interior maxillary wall extending from said second maxillary incremental platform;
a primary exterior mandibulary wall extending from said first mandibulary incremental platform;
a primary interior mandibulary wall extending from said first mandibulary incremental platform;
a secondary exterior mandibulary wall extending from said second mandibulary incremental platform;
a secondary interior mandibulary wall extending from said second mandibulary incremental platform;
a primary exterior hinge wall extending from said first hinge incremental platform;
a primary interior hinge wall extending from said first hinge incremental platform;
a secondary exterior hinge wall extending from said second hinge incremental platform;
a secondary interior hinge wall extending from said second hinge incremental platform;
a primary exterior hinge wall extending from said third hinge incremental platform;
a primary interior hinge wall extending from said third hinge incremental platform;
a secondary exterior hinge wall extending from said fourth hinge incremental platform;
a secondary interior hinge wall extending from said fourth hinge incremental platform;
said primary exterior maxillary wall abutting said primary exterior hinge wall of said first hinge, said primary interior maxillary wall abutting said primary interior hinge wall of said first hinge, said primary exterior mandibulary wall abutting said secondary exterior hinge wall of said first hinge and said primary interior mandibulary wall abutting said secondary interior hinge wall of said first hinge for defining a second griping mechanism and third griping mechanism respectively; and
said secondary exterior maxillary wall abutting said primary exterior hinge wall of said second hinge, said secondary interior maxillary wall abutting said primary interior hinge wall of said second hinge, said secondary exterior mandibulary wall abutting said secondary exterior hinge wall of said second hinge and said secondary interior mandibulary wall abutting said secondary interior hinge wall of said second hinge for defining a second griping mechanism and third griping mechanism respectively.

5. An anti-snoring and obstructive sleep apnea preventing device as set forth in claim 1, further including an anterior wall coupled to said upper maxillary member for contacting the upper jaw; and
a posterior wall coupled to said lower mandibulary member for contacting the lower jaw.

6. An anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining an airway passage, the device comprising:
an upper maxillary member defining a first general U-shape extending between a first end and a second end adapted to engage the maxillary dentition of the human;
a lower mandibulary member defining a second general U-shape extending between a first end and a second end adapted to engage the mandibulary dentition of the human;
a first maxillary incremental platform extending from said first end of said first general U-shape;
a second maxillary incremental platform extending from said second end of said first general U-shape;
a first mandibulary incremental platform extending from said first end of said second general U-shape;
a second mandibulary incremental platform extending from said second end of said second generally U-shape;
a first plurality of incremental mechanisms coupled to said first maxillary incremental platform;
a second plurality of incremental mechanisms coupled to said second maxillary incremental platform;
a third plurality of incremental mechanisms coupled to said first mandibulary incremental platform;
a fourth plurality of incremental mechanisms coupled to said second mandibulary incremental platform;
said first plurality of incremental mechanisms engaging with said third plurality of incremental mechanisms for defining a primary multiple stepwise snap on and snap off couple of said first end of said upper maxillary member with said first end of said lower mandibulary member;
said second plurality of incremental mechanisms engaging with said fourth plurality of incremental mechanisms for defining a secondary multiple stepwise snap on and snap off couple of said second end of said upper maxillary member with said second end of said lower mandibulary member;

a first hinge positioned adjacent to said primary multiple stepwise snap on and snap off couple for pivoting said first end of said upper maxillary member with said first end of said lower mandibulary member;

a second hinge positioned adjacent to said secondary multiple stepwise snap on and snap off couple for pivoting said second end of said upper maxillary member with said second end of said lower mandibulary member, said first hinge and said second hinge allowing movement of the lower jaw relative to the upper jaw; and said primary multiple stepwise snap on and snap off couple and said secondary multiple stepwise snap on and snap off couple defining a griping mechanism with an incremental adjustment for positioning said upper maxillary member relative to said lower mandibulary member between a neutral position and a maximum position and retaining a forward position of the lower jaw relative to the upper jaw for keeping the airway passage in the nasopharynx, the oropharynx and the hypopharynx substantially free of occlusions;

a primary exterior maxillary wall extending from said first maxillary incremental platform;

a primary interior maxillary wall extending from said first maxillary incremental platform;

a secondary exterior maxillary wall extending from said second maxillary incremental platform;

a secondary interior maxillary wall extending from said second maxillary incremental platform;

a primary exterior mandibulary wall extending from said first mandibulary incremental platform;

a primary interior mandibulary wall extending from said first mandibulary incremental platform;

a secondary exterior mandibulary wall extending from said second mandibulary incremental platform;

a secondary interior mandibulary wall extending from said second mandibulary incremental platform;

said primary exterior maxillary wall abutting said primary exterior mandibulary wall and said primary interior maxillary wall abutting said primary interior mandibulary wall for defining a second griping mechanism; and said secondary exterior maxillary wall abutting said secondary exterior mandibulary wall and said secondary interior maxillary wall abutting said secondary interior mandibulary wall for defining a third griping mechanism.

7. An anti-snoring and obstructive sleep apnea preventing device as set forth in claim 6, wherein said neutral position defines a first general ellipse with said upper maxillary member and said lower mandibulary member;

said maximum position defines a second general ellipse with said upper maxillary member and said lower mandibulary member; and said second general ellipse defining a greater area than said first general ellipse for retaining a forward position of the lower jaw relative to the upper jaw for keeping the airway passage in the nasopharynx, the oropharynx and the hypopharynx substantially free of occlusions.

8. An anti-snoring and obstructive sleep apnea preventing device as set forth in claim 6, wherein said first plurality of incremental mechanisms include a first plurality of holes;

said second plurality of incremental mechanisms include a second plurality of holes;

said third plurality of incremental mechanisms include a first plurality of knobs; and said fourth plurality of incremental mechanisms include a second plurality of knobs.

9. An anti-snoring and obstructive sleep apnea preventing device as set forth in claim 6, further including an anterior wall coupled to said upper maxillary member for contacting the upper jaw; and a posterior wall coupled to said lower mandibulary member for contacting the lower jaw.

10. An anti-snoring and obstructive sleep apnea preventing device for a human, the human having an upper jaw and a lower jaw, the upper jaw supporting a maxillary dentition, the lower jaw supporting a mandibulary dentition, the human having a nasopharynx, a oropharynx and a hypopharynx defining an airway passage, the device comprising:

an upper maxillary member adapted to engage the maxillary dentition of the human;

a lower mandibulary member adapted to engage the mandibulary dentition of the human;

said upper maxillary member and said lower mandibulary member defining a general ellipse;

a first end and a second end in said general ellipse;

a first incremental platform extending from said first end;

a second incremental platform extending from said second end;

a first plurality of incremental mechanisms coupled to said first incremental platform;

a second plurality of incremental mechanisms coupled to said second incremental platform;

said first plurality of incremental mechanisms engaging with said second plurality of incremental mechanisms for defining a multiple stepwise snap on and snap off couple of said first end and said second end;

a first hinge and a second hinge in said general ellipse for pivoting said upper maxillary member relative to end of said lower mandibulary member, said first hinge and said second hinge allowing movement of the lower jaw relative to the upper jaw;

said multiple stepwise snap on and snap off couple defining a griping mechanism with an incremental adjustment for positioning said upper maxillary member relative to said lower mandibulary member between a neutral position and a maximum position and retaining a forward position of the lower jaw relative to the upper jaw for keeping the airway passage in the nasopharynx, the oropharynx and the hypopharynx substantially free of occlusions;

said neutral position defines a first general ellipse area with said upper maxillary member and said lower mandibulary member;

said maximum position defines a second general ellipse area with said upper maxillary member and said lower mandibulary member;

said second general ellipse area defining a greater area than said first general ellipse area for retaining a forward position of the lower jaw relative to the upper jaw for keeping the airway passage in the nasopharynx, the oropharynx and the hypopharynx substantially free of occlusions;

a primary exterior maxillary wall extending from said first maxillary incremental platform;

a secondary exterior maxillary wall extending from said second maxillary incremental platform;

a primary exterior mandibulary wall extending from said first mandibulary incremental platform;

a secondary exterior mandibulary wall extending from said second mandibulary incremental platform;

said primary exterior maxillary wall abutting said primary exterior mandibulary wall for defining a second griping mechanism; and said secondary exterior maxillary wall abutting said secondary exterior mandibulary wall for defining a third griping mechanism.

* * * * *